United States Patent
Coates et al.

(10) Patent No.: US 6,852,865 B2
(45) Date of Patent: Feb. 8, 2005

(54) CATALYTIC CARBONYLATION OF THREE AND FOUR MEMBERED HETEROCYCLES

(75) Inventors: Geoffrey W. Coates, Ithaca, NY (US); Yutan D. Y. L. Getzler, Ithaca, NY (US); Peter Wolczanski, Ithaca, NY (US); Viswanath Mahadevan, Freeville, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/307,520

(22) Filed: Dec. 2, 2002

(65) Prior Publication Data

US 2003/0162961 A1 Aug. 28, 2003

Related U.S. Application Data

(60) Provisional application No. 60/336,170, filed on Dec. 6, 2001.

(51) Int. Cl.$^7$ ................... C07D 303/00; C07D 205/00; C07F 13/00
(52) U.S. Cl. ................ 548/950; 548/952; 548/953; 548/959; 548/965; 556/27; 556/45; 556/57; 556/76; 556/182; 549/88; 549/96; 549/510; 549/512; 502/161
(58) Field of Search ................ 549/88, 96, 510, 549/512; 556/27, 45, 57, 76, 182; 548/950, 952, 953, 959, 965; 502/161

(56) References Cited

U.S. PATENT DOCUMENTS 5,493,017 A * 2/1996 Therien et al. ............. 540/145
5,756,723 A * 5/1998 Therien et al. ............. 540/145

FOREIGN PATENT DOCUMENTS

WO   WO 03/011941 A2   2/2003

OTHER PUBLICATIONS

Ando et al, Stereochemistry of Vicinal Cyanohydrin Reduction–Elimination, Jol. Ameri. Chem. Soc. vol. 100 No. 11 pp 3615–361.*

Koda–Foldes, Current Organic Chemistry (2002), vol. 6 No. 12 pp. 1097–1119, "Synthetic applications of palladium catlysed carbonylation of organic halides".*

Calo et al, Journal of Organometallic Chemistry, vol. 645, Iss. 1–2, pp 152–157, (Feb. 5, 2002).*

Mori, Y., et al, Bulletin of the Chemical Society of Japan 42, 777–779 (1969).

* cited by examiner

Primary Examiner—Cecilia J. Tsang
Assistant Examiner—Raymond Covington

(57) ABSTRACT

Epoxides, aziridines, thiiranes, oxetanes, lactones, lactams and analogous compounds are reacted with carbon monoxide in the presence of a catalytically effective amount of catalyst having the general formula [Lewis acid]$^{z+}$\{[QM(CO)$_x$]$^{w-}$\}$_y$ where Q is any ligand and need not be present, M is a transition metal selected from the group consisting of Groups 4, 5, 6, 7, 8, 9 and 10 of the periodic table of elements, z is the valence of the Lewis acid and ranges from 1 to 6, w is the charge of the metal carbonyl and ranges from 1 to 4 and y is a number such that w times y equals z, and x is a number such as to provide a stable anionic metal carbonyl for \{[QM(CO)$_x$]$^{w-}$\}$_y$ and ranges from 1 to 9 and typically from 1 to 4.

87 Claims, 1 Drawing Sheet

CATALYTIC CARBONYLATION OF THREE AND FOUR MEMBERED HETEROCYCLES

CROSS-REFERENCE TO RELATED APPLICATION

This application claims the benefit of U.S. Provisional Application No. 60/336,170, filed Dec. 6, 2001, the whole of which is incorporated herein by reference.

FIELD OF INVENTION

This invention is directed to catalytic carbonylation of epoxides, aziridines, thiiranes, oxetanes, lactones, lactams and analogous compounds.

BACKGROUND OF THE INVENTION

Poly((R)-β-hydroxybutyrate), i.e., R-PHB, a naturally occurring thermoplastic polyester, shares many of the physical and mechanical properties of poly(propylene) but unlike polypropylene is biodegradable. Despite proven properties and ready applications, industrial production of R-PHB as a bulk polymer using biological methods has, to date, proven economically non-viable. Potential alternate synthetic routes to this promising polymer include Baeyer-Villiger oxidation of an isotactic propylene/carbon monoxide copolymer, asymmetric hydrogenation of the unsaturated polyester from ring opening polymerization (ROP) of ketene dimer, and ROP of (R)-β-butyrolactone (R-BBL). The first two routes involve post-polymerization modification of a polymer backbone, a difficult and unreliable task. The third route uses the proven technology of lactone polymerization but presently the starting material R-BBL is not a readily available commodity such as would be required for commercial polymer production. Thus, for commercial production of R-PHB by the third route, there is a need for an efficient, effective, inexpensive process for producing R-BBL.

The approach with the most promise for producing R-BBL is the catalytic synthesis of R-BBL from R-propylene oxide and carbon monoxide. R-Propylene oxide is readily available through Jacobsen's hydrolytic kinetic resolution as described in Tokunaga, M., et al., Science 277, 936–938 (1997).

Drent, E., et al. European Patent Application No. 0577206 is directed to a process for the carbonylation of expoxides by reaction with carbon monoxide at elevated pressure and temperature in the presence of a catalyst system comprising a source of cobalt and a hydroxy substituted pyridine compound. Data is presented in Example 5 of European Patent Application No. 0577206 where reaction pressurized to 60 bar carbon monoxide at 75° C. for 6 hours, is indicated to give 93% conversion of propylene oxide with a selectivity of greater than 90% into β-butyrolactone (BBL). However, Lee, T. L., et al., J. Org. Chem. 65, 518–521 (1999) and inventors herein were unable to produce the results of Drent and rather obtained low (15%) yields of BBL and significant amounts of undesired oligomeric by-products.

Lee, T. L., et al., J. Org. Chem. 64, 518–521 describes the carbonylation of propylene oxide using 900 psi CO at 80° C. in dimethoxyethane using a mixture of [$Ph_3P=N=PPh_3$] [$Co(CO)_4$] and $BF_3 \cdot EtO$ as a catalyst to obtain a yield of 77% BBL (some α-methyl-β-propiolactone also was produced) in a 24 hour reaction. This result leaves room for consideration of other catalyst systems.

SUMMARY OF THE INVENTION

It has been found herein that the catalytic activity of the catalyst system used for carbonylation of epoxides is mediated by modification of the cation therein and that use of a cationic Lewis acid as the cation in the catalyst system provides a novel approach. While the $BF_3$ in the catalyst of Lee et al. is a Lewis acid, it is a neutral Lewis acid. The cation in the Lee et al. catalyst system is [$Ph_3P=N=PPh_3$]$^+$ which is not a Lewis acid. It is possible that a cationic Lewis acid is formed in situ in the reaction described in Drent et al. European Patent Application No. 0577206. The instant invention does not embrace the Drent et al. catalytic system or any catalyst formed therefrom and in one subset embraces only formation of cationic Lewis acid extrinsic to the carbonylation reaction and charging substrate and catalyst and then reacting with carbon monoxide under pressure.

In a preferred embodiment herein, the catalyst system provides very high yields in short reaction time (e.g., yields greater than 95% BBL or R-BBL in less than 2½ hours).

Furthermore, it has been found that the catalyst system herein is useful not only for carbonylation of R-propylene oxide and propylene oxide but also for carbonylation of analogs of these and also for carbonylation of corresponding four membered heterocycles. BBL and said carbonylation products of analogs may be polymerized to form polymers which may be used as additives to R-PHB to modify the properties thereof. Furthermore, resulting chiral lactones, lactams, thiolactones, γ-lactones and anhydrides, etc. are useful in organic synthesis.

An invention of one embodiment herein, denoted the first embodiment, is directed to a process for carbonylation of a compound having the formula:

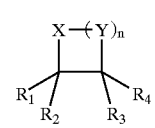

(I)

where $R_1$, $R_2$, $R_3$ and $R_4$ are selected from the group consisting of hydrogen, $C_1$–$C_{100,000}$-alkyl, $C_2$–$C_{100,000}$-alkenyl and $C_6$–$C_{100,000}$-aryl, where the alkyl, alkenyl and aryl are optionally substituted with halogen or benzyl ether, and alkylaryl, ester, ketone, alcohol, acid, aldehyde, amide and tosyl containing from 1 to 20 carbon atoms, and benzyl ether, alkyl substituted silyl ether where the ether group is $C_1$–$C_6$ alkylene and where the alkyl substitution consists of one to three $C_1$–$C_6$ alkyl(s) substituted on silyl, and any other functionality that the catalyst referred to below is tolerant of, and where where $R_2$ and $R_4$ can join to from a ring, and X is selected from the group consisting of O, S and $NR_5$ where $R_5$ is selected from the group consisting of hydrogen, $C_1$–$C_{100,000}$-alkyl, $C_2$–$C_{100,000}$-alkenyl and $C_6$–$C_{100,000}$-aryl where the alkyl, alkenyl and aryl are optionally substituted with halogen or benzyl ether, and alkylaryl, ester, ketone, alcohol, acid, aldehyde, amide and tosyl containing from 1 to 20 carbon atoms and benzyl ether, alkyl substituted silyl ether where the ether group is $C_1$–$C_6$-alkylene and where the alkyl substitution consists of one to three $C_1$–$C_6$ alkyl(s) substituted on silyl, and any other functionality that the catalyst referred to below is tolerant of and does not cause rearrangement and where n is 0 or 1, and Y is C=O or $CH_2$, said process comprising the step of reacting compound (I) with carbon monoxide in the presence of a catalytically effective amount of catalyst having the general formula [Lewis acid]$^{z+}${[$QM(CO)_x$]$^{w-}$}$_y$ where Q is any ligand and need not be present, M is a transition metal selected from the group consisting of transition metals of Groups 4, 5, 6, 7, 8, 9 and 10 of the periodic table of elements and z is the valence of the Lewis acid and ranges from 1 to 6, w is the charge of the metal carbonyl and ranges from 1 to 4 and is usually 1, y is a number such that w times y equals z and x is a number such as to provide a stable anionic metal carbonyl for $\{[QM(CO)_x]^{w-}\}_y$ and ranges from 1 to 9 and typically from 1 to 4, to form a product having the structural formula:

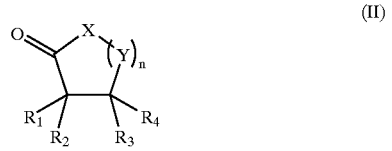

(II)

where $R_1$, $R_2$, $R_3$ and $R_4$ and X correspond to $R_1$, $R_2$, $R_3$, $R_4$ and X in (I) including $R_2$ and $R_4$ forming a ring if that is the case for (I), and in the case where n for (I) is 0, n for (II) is 0 or 1, and in the case where n for (I) is 1, n for (II) is 1; said catalyst excluding catalyst formed from the combination of a cobalt source and a hydroxy substituted pyridine.

The alkyls include branched as well as straight chain alkyls. $C_1$–$C_{100,000}$alkyl, $C_2$–$C_{100,000}$alkenyl and $C_6$–$C_{100,000}$aryl used in the definition of $R_1$, $R_2$, $R_3$, $R_4$ and $R_5$ allow for the heterocycles being pendant to polymers; where the heterocycles are not pendant to polymers, the range for alkyl can be, for example $C_1$–$C_{20}$, the range for alkenyl can be, for example, $C_2$–$C_{20}$, and the range for the aryl can be, for example, $C_6$–$C_{20}$.

The term "halogen" includes fluorine, chlorine, iodine and bromine.

The term "any other functionality that the catalyst referred to below is tolerant of" is used herein to mean that the functionality can be present without causing the catalyst to be inactive.

The term "does not cause rearrangement" excludes the case where one or more moieties, particularly $R_5$, become part of or the ring that is formed, e.g., in the case where $R_5$ is benzoyl as is demonstrated below, or otherwise change the order of connectivity inherent in the starting heterocycle excluding the insertion of C=O functionality as defined above.

The term "such as to provide a stable anionic metal carbonyl for $\{[QM(CO)_x]^{w-}\}_y$" is used herein to mean that $\{[QM(CO)_x]^{w-}\}_y$ is a species characterizable by analytical means, e.g., NMR, IR, X-ray crystallography, Raman spectroscopy and/or electron spin resonance (EPR) and isolable in catalyst form as the anion for a Lewis acid cation or a species formed in situ, excluding those that may result from the combination of a cobalt source, carbon monoxide and hydroxy substituted pyridines as set forth in Drent et al. European Patent Application No. 0577206.

In a subset of the invention of the first embodiment of the invention herein, at least one of $R_1$, $R_2$, $R_3$ and $R_4$ is not hydrogen.

In the subset of the first embodiment of the invention where n for (I) is 0 and n for (II) is 1, epoxide or analog is doubly carbonylated, arriving at the resultant anhydride or analog without the necessity of isolating the intermediate lactone or analog, thus providing a so called "one pot" reaction.

In a subset of the invention of the first embodiment of the invention herein, the catalyst is added catalyst, i.e., is not formed in situ in the carbonylation reaction.

A preferred catalyst has the structural formula:

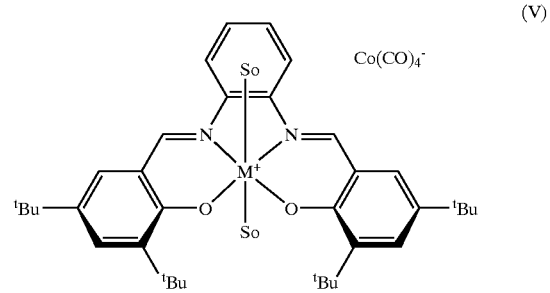

(V)

where So is tetrahydrofuran and $^t$Bu is t-butyl and M is Al or Cr. This catalyst where M is Al is referred to herein as Catalyst (G).

Another preferred catalyst has the structured formula:

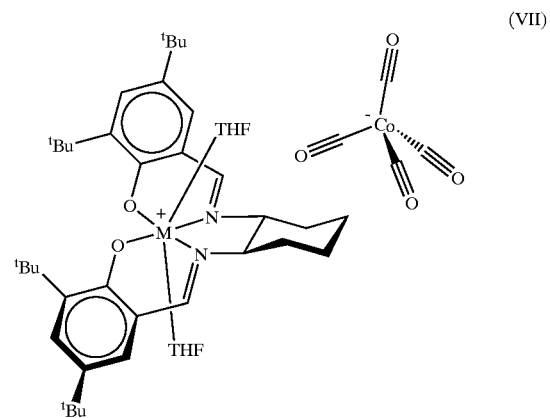

(VII)

where THF is tetrahydrofuran and $^t$Bu is t-butyl and M is Al or Cr. This catalyst where M is Al is referred to as catalyst ($E^1$).

Still another preferred catalyst has the structural formula:

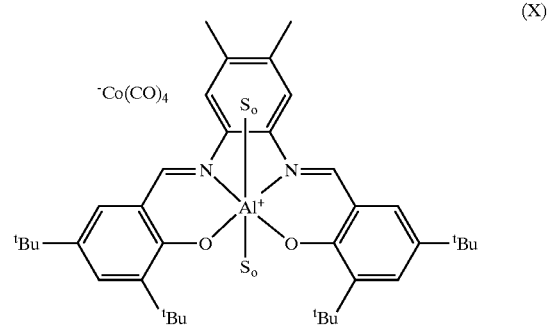

(X)

where So is tetrahydrofuran and $^t$Bu is t-butyl. This catalyst is referred to as catalyst (H).

Still another preferred catalyst has the structural formula:

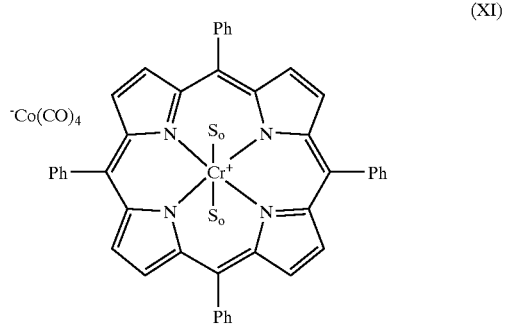

(XI)

where So is tetrahydrofuran and Ph is phenyl. This catalyst is referred to as catalyst (J).

Still another preferred catalyst has the structural formula:

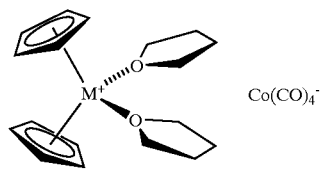

(VI)

where M is titanium with a valence of three. This catalyst is referred to as catalyst ($G^1$).

Still another preferred catalyst has the structured formula:

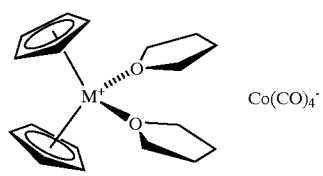

(VI)

where M is samarium with a valence of three. This catalyst is referred to as catalyst ($G^2$).

Another embodiment of the invention denoted the second embodiment is directed to the case where the compound carbonylated has the structural formula:

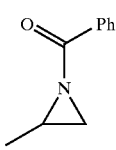

(XI)

where Ph is phenyl, and the process comprises the step of reacting compound (XI) with carbon monoxide in the presence of a catalytically effective amount of catalyst having the general formula $[\text{Lewis acid}]^{z+}\{[QM(CO)_x]^{w-}\}_y$ where Q is any ligand and need not be present, M is a transition metal selected from the group consisting of transition metals of Groups 4, 5, 6, 7, 8, 9 and 10 of the periodic table of elements and z is the valence of the Lewis acid and ranges from 1 to 6, w is the charge of the metal carbonyl and ranges from 1 to 4, and y is a number such that w times y equals z and x is a number such as to provide a stable anionic metal carbonyl for $\{[QM(CO)_x]^{w-}\}_y$ and ranges from 1 to 9 and typically from 1 to 4, to form a product which comprises a mixture of:

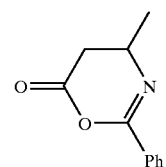

and

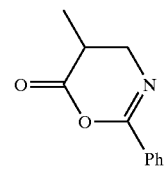

The compound (XI) has the structural formula (I) where n is 0, X is $NR_5$ and $R_5$ is benzoyl. In this case $R_5$ participates in rearrangement whereby the carbonyl of $R_5$ becomes part of the ring of the product and the Ph of $R_5$ becomes directly bonded to the ring of the product.

A third embodiment of the invention is directed to novel catalysts useful for carbonylation reactions of the first and second embodiments of the invention.

One genus of novel catalysts for the third embodiment comprises compounds having the structural formula:

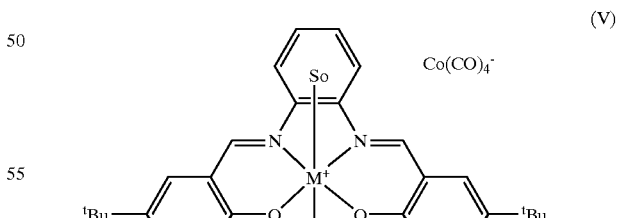

(V)

where $^t$Bu is t-butyl and M is Al or Cr and So is a neutral two electron donor. A preferred catalyst of this genus has the structural formula (V) where M is Al and the neutral two electron donor is tetrahydrofuran and is referred to as catalyst (G).

Another genus of novel catalysts for the third embodiment comprises compounds having the structural formula:

(VIII)

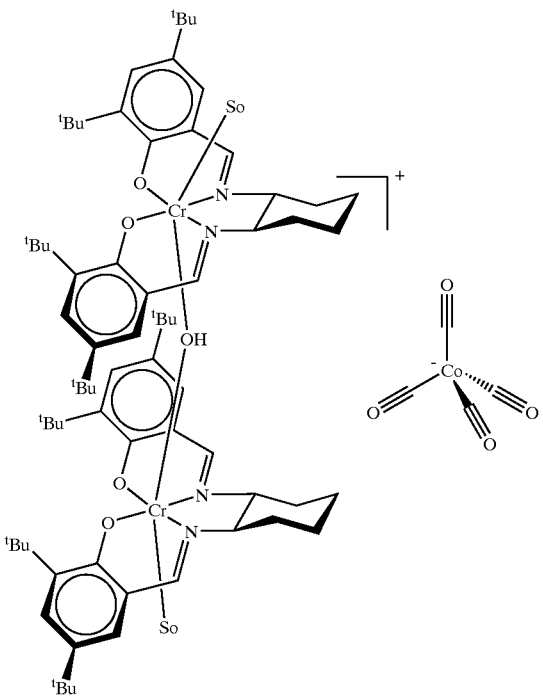

where $^{t}$Bu is t-butyl and So is a neutral two electron donor. A preferred catalyst of this genus has the structural formula (VIII) where the neutral two electron donor is tetrahydrofuran and is referred to as catalyst (B).

Another genus of novel catalysts for the third embodiment comprises compounds having the structural formula:

(IX)

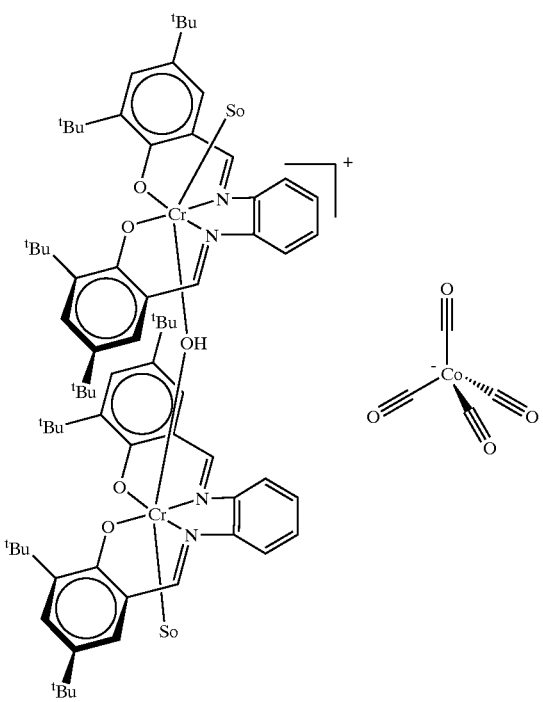

where $^{t}$Bu is t-butyl and So is a neutral two electron donor. A preferred catalyst of this genus has the formula (IX) where the neutral two electron donor is tetrahydrofuran and is referred to as catalyst (F).

Also included in the third embodiment is the compound having the structural formula:

(VII)

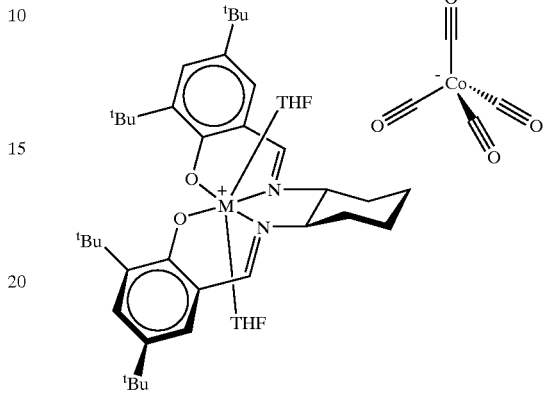

where $^{t}$Bu is t-butyl, THF is tetrahydrofuran and M is Al. This compound is referred to as catalyst ($E^1$).

Another genus of novel catalysts for the third embodiment comprises compounds having the structural formula:

(X)

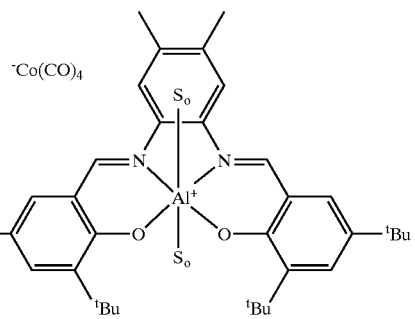

where $^{t}$Bu is t-butyl and So is a neutral two electron donor. A preferred catalyst of this genus has the structural formula (X) where the neutral two electron donor is tetrahydrofuran and is referred to as catalyst (H).

Still another genus of novel catalysts for the third embodiment comprises compounds having the structural formula:

(XI)

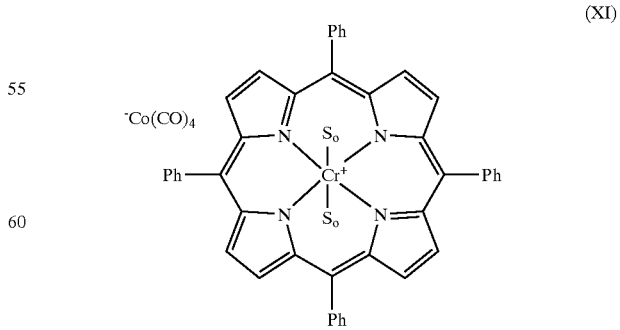

where Ph is phenyl and So is a two electron donor. A preferred catalyst of this genus has the structural formula (XI) where the neutral two electron donor is tetrahydrofuran and is referred to as catalyst (J).

Further variation of metal and ligand architecture will be obvious to those skilled in the art.

DETAILED DESCRIPTION

Figure 1:
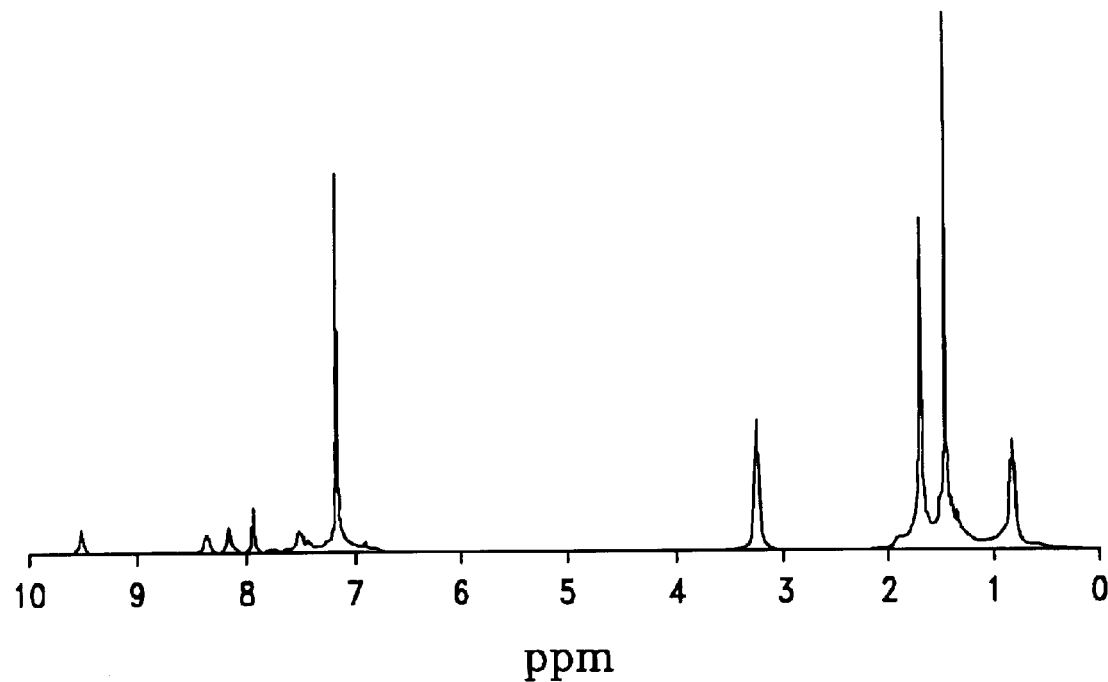
FIG. 1 shows NMR data for Catalyst (G); the y-axis for the figure is arbitrary intensity.

We turn now to the compound to be carbonylated in the first embodiment which has the formula:

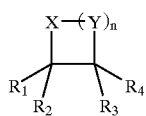
(I)

where $R_1$, $R_2$, $R_3$ and $R_4$ are selected from the group consisting of hydrogen, $C_1$–$C_{100,000}$-alkyl, $C_2$–$C_{100,000}$-alkenyl and $C_6$–$C_{100,000}$-aryl, where the alkyl, alkenyl and aryl are optionally substituted with halogen or benzyl ether, and alkylaryl, ester, ketone, alcohol, acid, aldehyde, amide and tosyl containing from 1 to 20 carbon atoms and benzyl ether, alkyl substituted silyl ether where the ether group is $C_1$–$C_6$ alkylene and where the alkyl substitution consists of one to three $C_1$–$C_6$ alkyl(s) substituted on silyl and any other functionality that the catalyst referred to below is tolerant of, and where $R_2$ and $R_4$ can join to form a ring and X is selected from the group consisting of O, S and $NR_5$ where $R_5$ is selected from the group consisting of hydrogen, $C_1$–$C_{100,000}$-alkyl, $C_2$–$C_{100,000}$-alkenyl, and $C_6$–$C_{100,000}$-alkyl where the alkyl, alkenyl and aryl are optionally substituted with halogen or benzyl ether, and alkylaryl, ester, ketone, alcohol, acid, aldehyde, amide and tosyl containing from 1 to 20 carbon atoms, and benzyl ether, alkyl substituted silyl ether where the ether group is $C_1$–$C_6$-alkylene and where the alkyl substitution consists of one to three $C_1$–$C_6$ alkyl(s) substituted on silyl, and any other functionality that the catalyst referred to below is tolerant of and does not cause rearrangement and where n is 0 or 1, and Y is C=O or $CH_2$.

We turn now to the examples of compound (I) where n is 0 and X is O, i.e., which are epoxides. The compound (I) of most interest herein is R-propylene oxide, i.e., compound (I) where X is O and $R_1$ is H, $R_2$ is H, $R_3$ is (R)-Me and $R_4$ is H, since carbonylation of that compound herein provides R-BBL. Other monocyclic epoxide compounds (I) herein include, for example, ethylene oxide (compound (I) where n is 0 and X is O and $R_1$ is H, $R_2$ is H, $R_3$ is H and $R_4$ is H), propylene oxide (compound (I) where n is 0 and X is O and $R_1$ is H, $R_2$ is H, $R_3$ is Me and $R_4$ is H); 1-butene oxide which also may be named 1,2-epoxybutane (compound (I) where n is 0 and X is O and $R_1$ is H, $R_2$ is H, $R_3$ is Et and $R_4$ is H); 1-heptene oxide (compound (I) where n is 0 and X is O and $R_1$ is H, $R_2$ is H, $R_3$ is $C_5H_{11}$ and $R_4$ is H); isobutylene oxide (compound (I) where n is 0 and X is O and $R_1$ is H, $R_2$ is H, $R_3$ is Me and $R_4$ is Me); 2,3-epoxybutane (compound (I) where n is 0 and X is O and $R_1$ is H, $R_2$ is Me, $R_3$ is Me and $R_4$ is H); epichlorohydrin (compound (I) where n is 0 and X is O and $R_1$ is H, $R_2$ is H, $R_3$ is $CH_2Cl$ and $R_4$ is H); and epibromohydrin (compound (I) where n is 0 and X is O and $R_1$ is H, $R_2$ is H, $R_3$ is $CH_2Br$ and $R_4$ is H); 1,2-epoxy-5-hexene (compound (I) where n is 0 and X is O and $R_1$ is H, $R_2$ is H, $R_3$ is H and $R_4$ is —$(CH_2)_2$ CH=$CH_2$); and benzyl glycidyl ether which has the formula:

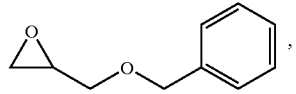

i.e., compound (I) where $R_1$ is H, $R_2$ is H, $R_3$ is $CH_2OCH_2Ph$ and $R_4$ is H. Examples of bicyclic epoxides for compound (I) include, for example, cyclohexene oxide (compound (I) where $R_1$ is H, $R_3$ is H, and $R_2$ and $R_4$ from —$(CH_2)$—$_4$, cyclopentene oxide (compound (I) where $R_1$ is H, $R_3$ is H and $R_2$ and $R_4$ form —$(CH_2)_3$—, cyclooctene oxide (compound (I) where $R_1$ is H, $R_3$ is H and $R_2$ and $R_4$ form —$(CH_2)_6$—) and cyclododecene oxide (compound (I) where $R_1$ is H, $R_3$ is H and $R_2$ and $R_4$ form —$(CH_2)_{10}$—). These monocyclic and bicyclic epoxides are all available commercially.

We turn now to examples of compound (I) where n is 0 and X is $NR_5$ where $R_5$ is selected from the group consisting of $C_1$–$C_{100,000}$-alkyl, $C_2$–$C_{100,000}$-alkenyl and $C_6$–$C_{100,000}$-aryl, where the alkyl, alkenyl and aryl are optionally substituted with halogen or benzyl ether, and alkylaryl, ester, ketone, alcohol, acid, aldehyde, amide and tosyl containing from 1 to 20 carbon atoms and benzyl ether, alkyl substituted silyl ether where the ether group is $C_1$–$C_6$-alkylene and where the alkyl substitution consists of one to three $C_1$–$C_6$ alkyl(s) substituted on silyl, and any other functionality that the catalyst referred to below is tolerant of and does not cause rearrangement. These compounds are aziridines. These include ethyl ethyleneimine, also denoted 2-ethylaziridine, (compound (I) where n is 0 and X is NH, $R_1$ is H, $R_2$ is H, $R_3$ is Et and $R_4$ is H) which is commercially available. Other aziridines useful herein, which are commercially available, are listed in Aldrichimica Acta 2001, 34(2); these are cis-2,3-diphenyl-1-propylaziridine; trans-2,3-diphenyl-1-propylaziridine; cis-1-isopropyl-2,3-diphenylaziridine; trans-1-isopropyl-2,3-diphenylaziridine; 2-methylaziridine; cis-1,2,3-triphenylaziridine; 1-azridineethanol; 1-benzyl 2-methyl (S)-(−)-1,2-aziridinecarboxylate; (S)-(+)-2-benzyl-1-(p-tolylsulfonyl) aziridine; methyl (S)-(−)-1-trityl-2-aziridinecarboxylate; and trimethylolpropane tris(2-methyl-1-aziridinepropionate). Another aziridine useful herein is 1-benzyl-2-methylaziridine, i.e., compound (I) where n is 0 and X is $NCH_2(C_6H_5)$, $R_1$ is H, $R_2$ is H, $R_3$ is H and $R_4$ is Me; this compound can be made as described in Piotti, M. E., et al, J. Am. Chem. Soc. 118, 111–116 (1996). Still another aziridine useful herein is 7-benzyl-7-azabicyclo [4.1.0]heptane; i.e., compound (I), where n is 0 and X is $NCH_2(C_6H_5)$, $R_1$ is H, $R_3$ is H and $R_2$ and $R_4$ are linked by —$(CH_2)_4$—; this compound is made in Background Example 1 hereinafter. Still another aziridine useful herein is 1-tosyl-2-methylaziridine (compound (I) where X is NOS (=O)$_2C_7H_8$, $R_1$ is H, $R_2$ is H, $R_3$ is H and $R_4$ is Me; this compound is made is Background Example 2 hereinafter. Still another aziridine useful herein is cis-1-benzyl-2-(tert-butyldimethylsilyloxymethyl)-3 aziridine (compound (I) where X is NH, $R_1$ is $CH_2C_5H_5$, $R_2$ is H, $R_3$ is H and $R_4$ is $CH_2OSi(CH_3)_2[C(CH_3)_3]$; this compound is made as described in Piotti, M. E., et al., J. Am. Chem. Soc. 118, 111–116 (1996). Other aziridines useful herein are available through well established synthetic routes, for example, from epoxides via ring opening with a primary amine and ring closure with ethyl diazoacetate or from alkanes with R—N=N—R' using a copper catalyst.

We turn now to examples of compounds (I) where n is 0 and X is S. These compounds are thiiranes. Thiiranes useful herein that are commercially available include aliphatic thiiranes that are commercially available in gram to kilogram quantities, e.g., propylene sulfide, epithiochlorohydrin and isobutylene sulfide. A number of other functionality substituted (i.e., esters, acids, amides, ketones, etc.) thiiranes are also available although many of those only in sub-gram quantities.

We turn now to examples of compounds (I) where n is 1 and X is O and Y is $CH_2$. These compounds are oxetanes. An oxetane useful herein has the structure (I) where n is 1 and Y is $CH_2$ and $R_1$, $R_2$, $R_3$ and $R_4$ are H and is denoted oxetane and is available commercially. Other oxetanes are commercially available or can be made by standard procedures in the chemical literature.

We turn now to examples of compounds (I) where X is O, n is 1 and Y is C=O. These compounds are lactones. Lactones useful herein include those having the structure (I) where X is O, n is 1 and Y is C=O where $R_1$, $R_3$ and $R_4$ are H and $R_2$ is Me, Et or $CCl_3$ or where $R_1$, $R_2$ and $R_4$ are H and $R_3$ is Me or Ph; these compounds are available commercially. Other lactones can be made by the process described herein or as described in references cited in Mahadevan, V., et al, Angew. Chem. Int. Ed. 41, No. 15, 2781–2784 (2002) and Getzler, Y. D. Y. L., et al, J. Am. Chem. Soc. 124, No. 7, 1174–1175 (2002).

We turn now to examples of compounds (I) where X is $NR_5$, n is 1 and Y is C=O. These compounds are denoted lactams. These compounds are commercially available or can be made by the process outlined herein or by other processes described in the chemical literature.

Compounds (I) where X is $NR_5$, n is 1 and Y is $CH_2$ are azetidines. The compound where $R_5$ is H, n is 1, Y is $CH_2$ and $R_1$, $R_2$, $R_3$ and $R_4$ are H is commercially available. Others can be synthesized.

Compounds (I) where X is S, n is 1 and Y is C=O are thiolactones. Synthesis of some of these can be carried out as described in the chemical literature.

Compounds (I) where X is S, n is 1 and Y is $CH_2$ are thietanes. The compound where X is S, n is 1, Y is $CH_2$ and $R_1$, $R_2$, $R_3$ and $R_4$ are H, is commercially available. Others can be synthesized.

We turn now to the processing conditions for the method of the first embodiment, i.e., the step of reacting the compound (I) with carbon monoxide in the presence of a catalytically effective amount of catalyst having the general formula $[\text{Lewis acid}]^{z+}\{[QM(CO)_x]^{w-}\}_y$ where Q is any ligand and need not be present, M is a transition metal selected from the group consisting of Groups 4, 5, 6, 7, 8, 9 and 10 of the periodic table of elements, z is the valence of the Lewis acid and ranges from 1 to 6, for example is 1 or 2, w is the charge of the metal carbonyl and ranges from 1 to 4 and usually is 1 and y is a number such that w times y equals z, and x is a number such as to provide a stable anionic metal carbonyl for $\{[QM(CO)_x]^{w-}\}_y$ and ranges from 1 to 9 and typically from 1 to 4.

The reaction equation is:

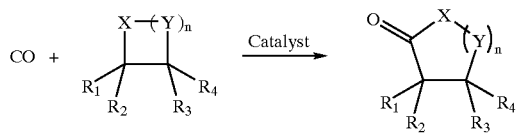

where $R_1$, $R_2$, $R_3$, $R_4$, X, Y and n are as defined above.

The reaction is carried out at a temperature ranging from 0° C. to 120° C., preferably from 40 to 80° C.

The mole ratio of CO to compound (I) should be at least 1:1 because of stoichiometry.

The reaction can be driven by a high concentration of CO. One way of accomplishing a high concentration of CO is to use high pressure CO, i.e., an amount of CO to impart a pressure ranging from 100 to 10,000 psi, preferably from 75 to 1,200 psi.

We turn now to the reaction catalyst. As indicated above, the reaction catalyst has the general formula $[\text{Lewis acid}]^{z+}\{[QM(CO)_x]^{w-}\}_y$ where Q is any ligand and need not be present, M is a transition metal selected from the group consisting of transition metals of Groups 4, 5, 6, 7, 8, 9 and 10 of the periodic table of elements, z is the valence of the Lewis acid and is 1 or 2, w is the charge of the metal carbonyl and ranges from 1 to 4 and usually is 1 and y is a number such that w times y equals z and x is a number such as to provide a stable anionic metal carbonyl for $\{[QM(CO)_x]^{w-}\}_y$ and ranges from 1 to 9 and typically from 1 to 4.

As indicated above, the catalyst in one subset is referred to as added catalyst. The term "added" means that the catalyst is formed extrinsic to the carbonylation reaction and is charged to the reaction before, during or after pressurization.

We turn now to the $[\text{Lewis acid}]^{z+}$, i.e., to the cationic Lewis acid portion of the catalyst. The term "Lewis acid" is used to mean an electron pair acceptor that can combine with a molecule or ion that is an electron pair donor forming either covalent or coordinative bond(s), and the term "cationic Lewis acid" is used to mean a Lewis acid that has one or more positive charges. Preferably, the cationic Lewis acid portion of the catalyst contains a metal, e.g., aluminum or chromium, and a neutral two electron donor which is coordinatively or covalently bound to the metal. The neutral two electron donor has the function of filling the coordination valence of the cationic Lewis acid. In the catalysts B, $E^1$, $E^2$, F, G, H and J made herein, the neutral two electron donor is tetrahydrofuran (THF) and is an artifact from the catalyst synthesis. Other neutral two electron donors for the cationic Lewis acid portion of the catalyst besides THF, include, for example, diethyl ether, acetonitrile, carbon disulfide or pyridine. In the catalyst synthesis, the neutral two electron donor can be provided as the reaction solvent which can be added before or with or after the other reactants but is preferably added so as not to disturb the air free environment which is preferred for catalyst synthesis. Cationic Lewis acid portion of catalyst without a neutral two electron donor is also possible and can be provided by synthesizing the catalyst in a reaction solvent which is not a neutral two electron donor providing solvent or by heating catalyst where the cationic Lewis portion of catalyst contains a neutral two electron donor.

We turn now to the anionic portion of the catalyst which is $\{[QM(CO)_x]^{w-}\}_y$ where Q is any ligand and need not be present, M is a transition metal selected from the group consisting of transition metals of Groups 4, 5, 6, 7, 8, 9 and 10 of the periodic table of elements, z is the valence of the Lewis acid and is 1 or 2 or more, w is the charge of the metal carbonyl and ranges from 1 to 4 and is usually 1, y is a number such that w times y equals z and x is a number such as to provide a stable anionic metal carbonyl for $\{[QM(CO)_x]^{w-}\}_y$ and ranges from 1 to 9 and typically from 1 to 4. When Q is not present, the metals of Groups 7 and 9 are preferred. The metals of Group 7 include, for example, manganese. The metals of Group 9 include cobalt, rhodium and iridium. A very preferred metal M is cobalt. We turn now to the optional constituent Q which is any ligand; the term "ligand" is used to mean any discrete species that could have existence separate from the transition metal M. Suitable constituents Q include, for example, triphenylphosphine, cyclopentadienyl (Cp), and pentamethyl cyclopentadienyl (Cp*). Ligated metal carbonyl anions are readily accessible, in one step through well-known chemistry, e.g., by reduction of $Co_2(CO)_8$ which is commercially available.

The reaction catalysts are preferably formed in an air-free environment using standard glovebox and Schlenk-type techniques.

The catalysts where w is 1 and y is equal to z and z is 1 are formed by the reaction of [Lewis acid]-X with [QM(CO)$_x$]—Y where X is any leaving group and Y is a moiety that will form a salt with X or, alternatively, the catalysts where z ranges from 1 to 6, for example is 1 or 2, are formed from a redox reaction of [Lewis acid$^m$] and $z/2Q_2M_2(CO)_{2x}$ to form [Lewis acid$^{(m+z)}$]$^{z+}${[QM(CO)$_x$]$^-$}$_z$ where m is the oxidation state of the metal, z is both the valence of the Lewis acid and the number of anions associated with it and ranges from 1 to 6, for example is 1 or 2, M is a transition metal selected from the group consisting of transition metals of Groups 4, 5, 6, 7, 8, 9 and 10 of the periodic table of elements, and x is the number required to form a stable anionic carbonyl for {[QM(CO)$_x$]$^-$}$_z$. Complexes of the type [QM(CO)$_x$]—Y can be made by the reduction of the anionic species [QM(CO)$_x$]$_2$ where Q, M and x are as defined for {[QM(CO)$_x$]$^-$}$_z$. The species [QM(CO)$_x$]$_2$ in many cases are commercially available. Reducing agents include sodium amalgam and as described in Edgell, W. F., et al., Inorg. Chem. 1970, 9, 1932–1933, sodium hydroxide. This method was used in the synthesis of catalyst D (Catalyst Making 3, hereinafter).

One genus of preferred catalysts herein have the structure:

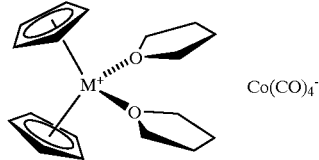

(VI)

where M is a metal such that (VI) is stable where stable means that the catalyst remains active for the course of the reaction. M can be, for example, titanium with a valence of 3 (catalyst (G$^1$)), samarium with a valence of 3 (catalyst (G$^2$)), lanthanum with a valence of 3 or hafnium with a valence of 3. Catalyst (G$^1$) can be made as described in Merola, J. S., et al. Inorg. Chem 28, 2950–2954 (1989) as well as Merola, J. S., et al., Inorg. Chim. Acta 165, 87–90 (1989). Catalyst (G$^2$) can be made as described in Evans, W. J., et al., Inorg. Chem. 24, 4620–4623 (1985) as well as, in Evans., W. J., et al., J. Am. Chem. Soc 107, 941–946 (1985). Other catalysts (VI) can be made in corresponding fashion.

Another catalyst herein is catalyst (G) described above. The synthesis of catalyst (G) is described in Catalyst Making Example 1 hereinafter. Catalyst (G) may be referred to as [(salph)Al(THF)$_2$][Co(CO)$_4$] where salph is N,N'-bis(3,5-di-tert-bulylsalicylidene)-1,2-phenylenediamimo.

Other catalysts for use herein are the catalysts denoted herein as catalysts B, D, E$^1$, E$^2$, F, H and J.

Catalyst (B) has the formula:

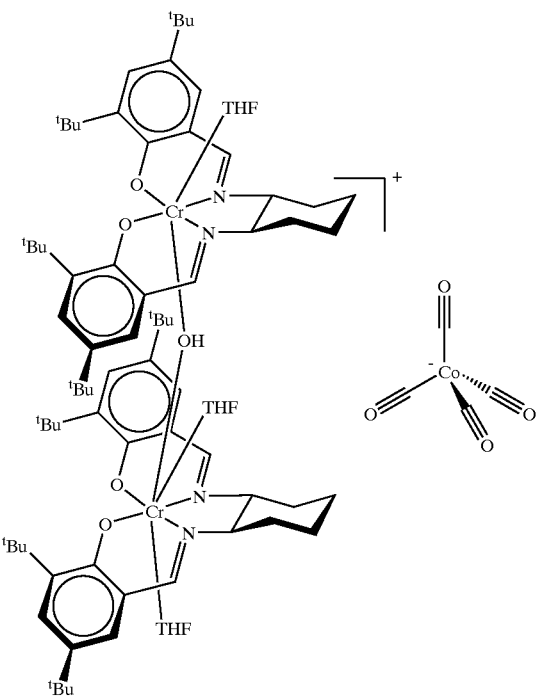

where THF is tetrahydrofuran and $^t$Bu is t-butyl. The synthesis of Catalyst (B) is described in Catalyst Making Example 2 hereinafter. Catalyst (B) was very active but its synthesis as described in Catalyst Making Example 2, has been difficult to replicate. An alternative route is the route to make catalyst (F) which is described in Background Example 6 hereinafter.

Catalyst (D) has the formula [Na]$^+$[Co(CO)$_4$]$^-$. The synthesis of Catalyst (D) is described in Catalyst Example 3 hereinafter.

Catalysts (E$^1$) and (E$^2$) have the formula:

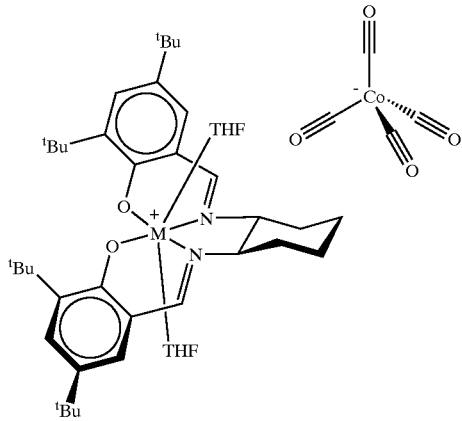

where THF is tetrahydrofuran and $^t$Bu is t-butyl and M is Al for Catalyst (E$^1$) and M is Cr for Catalyst (E$^2$). The synthesis of Catalyst (E$^1$) is described in Catalyst Making Example 4 hereinafter. The synthesis of Catalyst (E$^2$) is described in Catalyst Making Example 5 hereinafter.

Catalyst (F) has the formula:

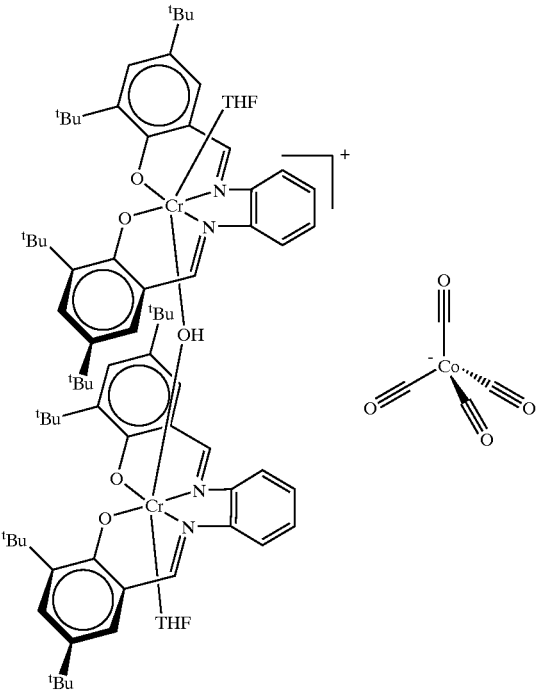

where THF means tetrahydrofuran and $^tBu$ is t-butyl. The synthesis of catalyst (F) is described in Catalyst Making Example 6 hereinafter.

Catalyst (H) has the formula:

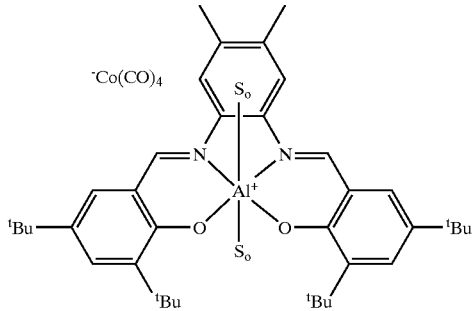

where So is tetrahydrofuran and $^tBu$ is t-butyl. The synthesis of Catalyst (H) is described in Catalyst Making Example 7 hereinafter.

Catalyst (J) has the formula:

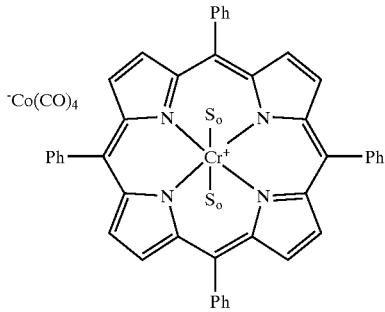

where So is tetrahydrofuran and Ph is phenyl. The synthesis of catalyst (J) is described in Catalyst Making Example 8 hereinafter.

An example of a catalyst where z is 2 is $[(salen)M]^{2+}[Co(CO)_4]_2^-$ where salen is any tetracoordinate dianionic ligand synthesized from a diamine and two equivalents of a 2-hydroxybenzaldehyde, which can be made from reaction of one equivalent of $(salen)Sn^{(II)}$ with one equivalent of $Co_2(CO)_8$ and M is a metal. The $(salen)Sn^{(II)}$ is readily obtainable from $[(Me_3Si)_2N]_2$ Sn and $(salen)H_2$ where $(salen)H_2$ is the protonated form of the ligand as shown in Kuchta, et al., J. C. S. Dalton Trans. 20, 3559 (1999).

For the catalysts $[Lewis\ acid]^{z+}\{[QM(CO)_x]^{w-}\}_y$, other Lewis acids besides what are illustrated above and their synthesis, will be obvious to those skilled in the art.

The mole ratio of compound (I) charged to catalyst charged, can range, for example, from 1:1 to 10,000:1 and preferably is 100:1 to 2,000:1 and the best ratio envisioned is 1,000:1. A mole ratio of 100:1 was found to give the best conversions but approximately 1,800:1 gives much better activity.

We turn now to the solvent for the reaction. The reaction may be carried out neat, i.e., without added solvent and where the compound (I) is the reaction vehicle to reduce waste disposal requirements as well as to simplify purification. If the reaction is not carried out neat, it may be carried out in diglyme, triglyme, dimethoxyethane (denoted DME hereinafter), or preferably in tetrahydrofuran, or may be carried out in any solvent in which catalyst, substrate and product are all soluble.

In the case where the compound (I) is a monocyclic epoxide and a single carbonyl is introduced, the reaction product of interest is a β-lactone. The terminology "β-lactone" is because the lactone can be formed by dehydrative lactonization of a β-hydroxy acid. In the case where the epoxide is bicyclic, there is no common name such as β-lactone and IUPAC would name the product according to bicyclic nomenclature. For example, the product of the carbonylation of cyclohexene oxide would be called 7-oxa-bicyclo[4.2.0]octan-8-one. The products of carbonylation of cyclooctene oxide and cyclododecene oxide are respectively called 9-oxa-bicyclo[6.2.0]decan-10-one and 13-oxa-bicyclo[10.2.0]tetradecan-14-one and are products made in carbonylation Examples XLI and XLII and are embodiments of the invention herein.

In the case where the compound (I) is a monocyclic aziridine and a single carbonyl is introduced, the reaction product of interest is a β-lactam.

In the case where the compound (I) is a monocyclic oxetane, the reaction product of interest is a γ-lactone.

In the case where the compound (I) is a monocyclic thiirane and a single carbonyl is introduced, the reaction product of interest is a thiolactone.

In the case where the compound (I) is a monocyclic lactone, the reaction product of interest is a cyclic acid anhydride.

In the case of the compound (I) where X is $NR_5$, n is 1 and Y is $CH_2$ and the compound (I) is monocyclic, i.e., where the compound (I) is a monocyclic azetidine, the reaction product of interest is a γ-lactam.

In the case of the compound (I) where X is $NR_5$, n is 1 and Y is C=O and the compound (I) is monocyclic, i.e., where the compound (I) is a monocyclic β-lactam, the reaction product of interest is a 2,5-pyrrolidinedione.

In the case where the compound (I) where X is S, n is 1 and Y is C=O and the compound is monocyclic, i.e., where the compound (I) is a monocyclic thiolactone, the reaction product of interest is a cyclic anhydrosulfide.

In the case of the compound (I) where X is S, n is 1 and Y is CH₂ and the compound (I) is monocyclic, i.e., where the compound (I) is a monocyclic thietane, the reaction product of interest is γ-thiolactone.

The yield of product of interest is determined from two components, i.e., the percent of compound (I) consumed, and the percent selectivity which is product of interest as a percentage of all products, and the percent conversion times percent selectivity gives yield percent. The yield percents obtained were related to catalyst and compound (I). For propylene oxide and R-propylene oxide, catalyst (G) give percents conversion of 95% with selectivity greater than 99%. For propylene oxide, Catalyst (B) gives percent conversion of 99% and percent selectivity greater than 99%.

The time of reaction is a parameter affecting percent yield. In general, times of reaction can range, for example, from 15 minutes to 96 hours. The preferred time of reaction for Catalyst (G) is one-half to 2 and one-half hours except where compound (I) was epichlorohydrin a time of 8–12 hours was more appropriate.

We turn now to the case where n for (I) is 0 and n for (II) is 1, and epoxide or analog is doubly carbonylated arriving at the resultant anhydride without the necessity of isolating the intermediate lactone or analog, thus providing a so-called "one pot" reaction. The reaction condition mainly affecting this is time of reaction. In other words, sufficient time is provided for a first carbonylation reaction to proceed to a finish whereupon sufficient further time is provided for the second carbonylation to be effected. Also reaction temperature, mole percent catalyst, catalyst used, substrate used and solvent, could influence conversion and selectivity.

The β-lactone products can be converted to polymers with metal alkoxide catalysts. See R, L. R., et al, J. Am. Chem. Soc. 2002, paper accepted for publication. See also Muller, H. M., et al., Angew. Chem. Int. Ed. Engl. 1993, 32, 477–502 and references cited therein. See also the following in respect to polymerization of β-lactones: Kurcok, P., et al., Macromolecules 1992, 25, 2017–2020; Hori, Y., et al., Macromolecules 1993, 26, 5533–5534; Le Borgne, A., et al., Macromol. Rapid Commun. 1994, 15, 955–960; Lenz, R. W., et al., Can. J. Microbiol. 1995, 41, 274–281; Cheng, M., et al., J. Am. Chem. Soc. 1998, 120, 11018–11019; and Schechtman, L. A., et al., J. Polym. Prepr. (Am. Chem. Soc., Div. Polym. Chem.) 1999, 40(1), 508–509.

The utility of the product from polymerization of R-BBL, namely R-PHB, is described above. Copolymers with lactones other than R-BBL give the ability to mediate the properties of the resultant polymer, e.g., plasticity, barrier properties and rate of degradation. The lactones, particularly chiral lactones, are also useful as synthetic intermediates in organic chemistry (e.g., see Gellman, S. H., Chem. Res. 31, 173 (1988); and Seebach, D., et al., Chem. Commun. 2015 (1997) which refers to chiral lactones as aldol analogs.

The lactam products can he converted to polymers with metal anion or metal amide catalysts. The polymers are called poly(lactam)s and have also been called poly-beta-peptides, and have been discussed in the literature as "biomimetic materials." See, for example, Magriotis, P. A., Angew. Chem. Int. Ed. Engl. 2001, Vol. 40, 4377–4379.

Products from polymerization of lactams, have utility, for example, for drug delivery. The lactams themselves may be used in antibiotics.

The thiolactone products (also called 4-alkyl-thietan-2-ones) can be converted to polymers or copolymers. For example, a copolymer of BBL and 3-mercaptopropionate (the thiolactone from the carbonylation of ethylene sulfide) can be prepared; the copolymer has modified properties from those of poly(β-hydroxybutyrate).

The γ-lactone and anhydride products for carbonylation of compound (I) where n=1 and analogs thereof have utility for the field of chemistry.

We turn now to the second embodiment of the invention herein which is directed to a process for the carbonylation of a compound having the formula:

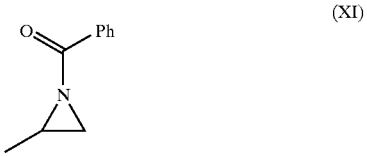

(XI)

said process comprising the step of reacting compound (XI) with carbon monoxide in the presence of a catalytically effective amount of catalyst having the general formula [Lewis acid]$^{z+}${[QM(CO)$_x$]$^{w-}$}$_z$ where Q is any ligand and need not be present, M is a transition metal selected from the group consisting of transition metals of Groups 4, 5, 6, 7, 8, 9 and 10 of the periodic table of elements and z is the valence of the Lewis acid and ranges from 1 to 6, for example is 1 or 2, w is the charge of the metal carbonyl and ranges from 1 to 4 and is usually 1 and y is a number such that w times y equals z and x is a number such as to provide a stable anionic metal carbonyl for {[QM(CO)$_x$]$^{w-}$}$_y$. The reaction is carried out at a carbon monoxide pressure ranging from 100 to 10,000 psi, preferably from 75 to 1,200 psi and a temperature ranging from 0° C. to 120° C., preferably from 40 to 80° C., in the presence of catalyst in a mole ratio of the compound (XI) to catalyst ranging from 1:1 to 10,000:1, preferably from 100:1 to 2000:1, for example over a time period ranging from 15 minutes to 96 hours. The catalysts useful for the second embodiment are the same as those useful for the first embodiment. The preferred catalyst for use in the second embodiment has been found to be Catalyst (G¹). The product comprises a mixture of the two isomeric oxazinones, namely 4-methyl-2-phenyl-4,5-dihydro-[1,3]oxazin-6-one which has the formula:

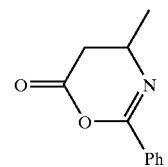

and 5-methyl-2-phenyl-4,5-dihydro-[1,3]oxazin-6-one which has the formula:

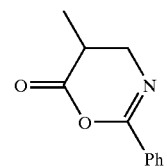

Thus, the benzoyl substituent on the aziridine participates in rearrangement to introduce the benzoyl into the ring of the product where the oxygen of the benzoyl becomes a ring atom and the double bond of the carbonyl of the benzoyl becomes part of the ring and the phenyl of the benzoyl is directly bonded to a ring carbon atom.

We turn now to the third embodiment of the invention herein. Catalysts the same as catalyst (B), (E¹), (F), (G), (H) and (J) but with different neutral two electron donor from THF can be prepared the same as the corresponding catalysts with THF by synthesizing the catalyst by method comprising adding source of different neutral two electron donor (e.g., diethyl ether, acetonitrile, carbon disulfide or pyridine) instead of THF for reaction of [Lewis acid]-X and [QM(CO)$_x$]—Y in the general reaction described above.

The following background Examples 1 and 2 illustrate the synthesis of compound (I) for use in the Reaction Examples XXIII and XXIV. The following Catalyst Synthesis Examples 1–8 illustrate making of the catalysts used in Reaction Examples and synthesis of catalysts of the third embodiment herein. Catalyst (H) used in Reaction Examples was made as described in Merola, J. S., et al., Inorg. Chem. 28, 2950–2954 (1989). Catalyst (J) used in a Reaction Examples hereinafter was made as described in Evans, W. J., et al, Inorg. Chem. 24, 4620–4623 (1985).

The following working Examples I–XLIII and associated tables, illustrate the methods herein.

BACKGROUND EXAMPLE 1

Synthesis of 7-Benzyl-7-Azabicyclo[4.1.0]heptane a) Synthesis of 2-Benzylamino-cyclohexanol. To a solution of cyclohexene oxide (5 g, 51 mmol) in 10 ml CH$_3$CN, anhydrous LiClO$_4$, (5.44 g., 51 mmol) was added and stirred until complete dissolution of the salt occurred. The resulting solution was treated with the required amount of benzylamine (5.5 g, 51 mmol) at room temperature with stirring. The reaction mixture was then stirred for 24 h at room temperature. At the end of the reaction, 100 ml water was added and the solution stirred for 30 min, extracted into diethyl ether (3×25) and finally crystallized from hot hexanes. (5.0 g, 50% yield).

$^1$H NMR (CDCL$_3$, 300 MHz): δ 0.93–1.10 (1H, m), 1.18–1.33 (4H, m), 1.71 (2H, m), 2.05 (1H, m), 2.15 (1H, m), 2.31 (1H, m), 3.20 (1H, m), 3.35 (1h, br), 3.68 (1H, d, J=12.9 Hz), 3.95 (1H, d, J=13.0 Hz), 7.23–7.35 (5H, m).

b) Cyclization of 2-Benzylamino-cyclohexanol. Diethyl azodicarboxylate (Aldrich, 95%, 3.6 ml, 22.6 mmol) was slowly added to an ether solution (50 ml) of 2-benzylaminio-cyclohexanol (3.1 g, 15 mmol) and PPh$_3$ (5.94 g, 22.6 mmol) under N$_2$, with stirring, in an ice-bath. After addition, the ice bath was removed, and the mixture stirred at room temperature for 36 h. The resulting crystalline precipitate was filtered and the solvent removed from the filtrate by rotary evaporation to yield the crude product, which was purified by column chromatography (petroleum ether: diethyl ether=50:50) (2.1 g, 75% yield).

$^1$H NMR (CDCl$_3$, 300 MHz): δ 1.31 (4H, m), 1.63 (2H, m), 1.83 (4H, m), 3048 (2H, s), 7.31 (5H, m).

BACKGROUND EXAMPLE 2

Synthesis of 2-Methyl-1-Tosyl-Aziridine

2-Methylaziridine (3.6 ml, 51 mmol) was added to a 10% aqueous KOH solution (30 ml) and cooled in an ice bath for 30 min. To this solution p-toluenesulfonyl chloride (9.9 g, 52 mmol) was added rapidly while maintaining the temperature below 4° C. The resulting mixture was stirred for 30 min at 0° C., then stirred at room temperature overnight. The white precipitate was washed multiple times with cold water and dried under vacuum. The washed product was dissolved in hot petroleum ether and allowed to crystallize at 0° C., yielding colorless crystals (6.3 g, 57% yield).

$^1$H NMR (CDCl$_3$, 300 MHz): δ 1.26 (3H, d, J=6.0), 2.02 (1H, d, J=4.5 Hz), 2.44 (3H, s), 2.58 (1H, d, J=6.9 Hz), 2.82 (1H, m), 7.31 (2H, d, J=8.1 Hz), 7.80 (2H, d, J=8.1 Hz).

CATALYST SYNTHESIS EXAMPLE 1

Synthesis of Catalyst (G)

All manipulations were performed with strict air-free techniques. All reagents and solvent were dried and degassed prior to use. In a drybox, N,N'-bis(3,5-di-tert-butylsalicylidene)-1,2-phenylenediamine (1.38 g, 2.55 mmol) was placed in a Schlenk tube equipped with a stir-bar and an air-free addition funnel charged with diethyl aluminum chloride (Aldrich, 1.8 M in toluene) (1.42 ml, 2.5 mmol). Upon removal to the bench top, the ligand was dissolved in 20 ml of CH$_2$Cl$_2$, giving a pale orange solution. Dropwise addition of diethyl aluminum chloride solution at room temperature resulted in considerable evolution of gas, which was vented, and a yellowing of the solution. After rinsing of the addition funnel several times with CH$_2$Cl$_2$, the solution was stirred for 8.5 hours during which a copious amount of yellow precipitate formed. In vacuo solvent removal gave a yellow solid which was rinsed 3–4 times with hexanes (10–20 ml) and then pumped down. The Schlenk tube was brought into a drybox where white powdery sodium cobalt tetracarbonyl (0.49 g, 2.53 mmol), stored at −35° C. under nitrogen, was added. Upon removal to the bench and addition of tetrahydrofuran (30 ml) at room temperature, the solution immediately turned a deep red. The foil wrapped tube stirred for two days and was concentrated to 5–10 ml, layered with hexanes (50 ml) and left to sit for a day. Significant amounts of yellow and white precipitates as well as masses of X-ray quality red crystals formed. The red crystals were the desired product, Catalyst (G). The impurities were easily washed away with repeated rinses of hexanes allowing isolation of pure catalyst [(salph) Al(THF)$_2$][Co(CO)$_4$], (G) (2.10 g, 93% yield).

$^1$H NMR (C$_6$D$_6$, 300 MHz) δ 9.53 (s, HC=N), 8.35 (s, HAr), 8.14 (s, HAr), 7.92 (s, HAr), 7.50 (s, HAr), 7.16 (s, HC$_6$D$_5$), 3.23 (s, O—CH$_2$), 1.70 (s, C(CH$_3$)$_3$), 1.46 (s, C(CH$_3$)$_3$), 0.83 (s, OCH$_2$CH$_2$), spectrum shown in FIG. 1. IR (KBr): ν$_{co}$=1885 cm$^{-1}$. Crystal data: triclinic, a=12.0136 (6) Å, b=13.2447(7) Å, c=15.2876(8) Å, α=101.560(1)°, β=91.506(1)°, γ=90.295(1)°, V=2382.1(2) Å$^3$, space group P-1; Z=2, formula weight 880.91 for C$_{40}$H$_{46}$AlCoN$_2$O$_4$.2C$_4$H$_8$O and density (calc.)=1228 g/ml; R(F)=0.0553 and Rw(F)=0.1474 (I>2σ(I)).

CATALYST SYNTHESIS EXAMPLE 2

Synthesis of Catalyst (B)

In a glovebox, a Schlenk tube was charged with 2.58 g (4.73 mmol) (R,R)-(−)-N,N'-bis(3,5-di-tert-butylsalicylaldehyde)-1,2-cyclohexanediamine, 0.615 g (5.01 mmol) of chromium (II) chloride (Strem, 99.9% anhydrous, used as received) and a teflon-coated magnetic stir-bar. THF was canulated in and the reaction was left stir for 6 hours at which point it was opened to the air and left to stir for 12 hours. The resultant cloudy brown-red solution was rinsed into a separatory funnel with 500 ml tert-butyl methyl ether, washed four times with 300 ml saturated ammonium chloride and four times with 300 ml saturated sodium chloride. The solution was dried with sodium sulphate, rotovaped to a red solid and recrystallized from acetonitrile to give 1.33 g (43% yield) of large red diamond shaped crystals Compound (C) which were characterized by IR and X-ray crystallography. Compound (C) was determined to have the structure:

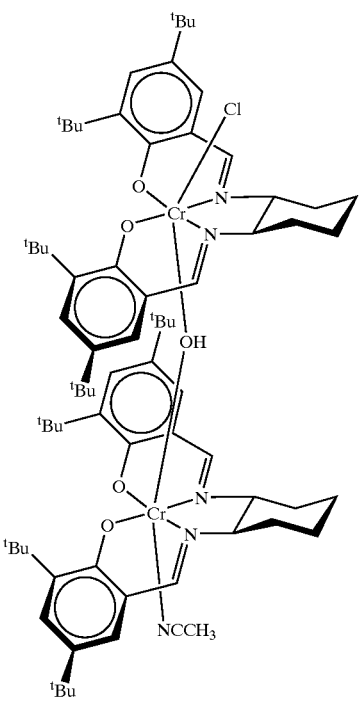

In a glovebox, a Schlenk tube was charged with 1.03 g (0.80 mmol), Compound C, 0.32 g (1.65 mmol) NaCo(CO)$_4$ (Catalyst(D)) and a teflon-coated magnetic stir-bar. THF was canulated in, the tube was covered in foil and the solution was left to stir for three days at which time it was concentrated in vacuao. Hexanes were layered on top of the dark red solution and the solution was left to sit for six day, although crystals had began to form within a day. A flocculent yellowish-white precipitate was separated from the large red blocks of crystals by repeated washing with hexanes. Isolation gave 1.14 g (88% yield) of pure Catalyst (B) which was characterized by IR and X-ray crystallography.

CATALYST SYNTHESIS EXAMPLE 3

Synthesis of Catalyst (D)

Catalyst (D) was synthesized as described in Edgell, W. F., et al., Inorg. Chem. 1970, 9, 1932–1933.

CATALYST SYNTHESIS EXAMPLE 4

Synthesis of Catalyst (E$^1$)

Synthesis of Catalyst (E$^1$) differs from that of Catalyst Synthesis Example 1 in one aspect only; in this synthesis (R,R)-(−)-N,N'-bis(3,5-di-tert-butylsalicylaldehyde)-1,2-cyclohexanediamine was used instead of N,N'-bis(3,5-di-tert-butylsalicylaldehyde)-1,2-phenylenediamine.

CATALYST SYNTHESIS EXAMPLE5

Synthesis of Catalyst (E$^2$)

In a glovebox, a Schlenk tube was charged with 0.64 g (1.06 mmol) (R,R)-(−)-N,N'-bis(3,5-di-tert-butylsalicylaldehyde)-1,2-cyclohexanediaminochromium (III) chloride (Aldrich), 0.21 g (1.06 mmol) NaCo(CO)$_4$ (Catalyst (D)) and a teflon-coated magnetic stir-bar. THF was canulated in, the tube was covered in foil and the solution was left to stir for two days at which time it was concentrated in vacuo. Hexanes were layered on top of the dark red solution and the solution was left to sit for six day, although crystals had began to form within a day. A flocculent yellowish-white precipitate was separated from the large red blocks of crystals by repeated washing with hexanies. Isolation gave 0.52 g (60% yield) of pure Catalyst (E$^2$) which was characterized by IR and X-ray crystallography.

CATALYST SYNTHESIS EXAMPLE 6

Synthesis of Catalyst (F)

In a glovebox, a Schlenk tube was charged with 0.28 g (0.51 mmol) N,N'-bis(3,5-di-tert-butylsalicylaldehyde)-1,2-phenylenediamine, 0.21 g (5.18 mmol) sodium hydride and a teflon-coated magnetic stir-bar. THF was canulated in with considerable ebullition. The headspace was removed and the solution was stirred at 50° C. for 22 hours at which point the excess sodium hydride was filtered off, using air-free technique, and the solution added to a Schlenk tube charged with 0.07 g (0.55 mmol) chromium (II) chloride and a teflon-coated magnetic stir-bar. The headspace was removed and the solution heated at 50° C. for 6 hours at which point the dark brown solution was filtered, to remove any NaCl, into a Schlenk tube charged with 0.09 g (0.26 mmol) dicobalt octcarbonyl and a teflon-coated magnetic stir-bar and stirred for 24 hours. The volume of solution was reduced in vacuo and hexanes layered on top. After two weeks the dark red crystals were isolated canulating off the mother liquor and washing the remaining material with copious amounts of hexanes resulting in the isolation of 0.26 g (70% yield) of Catalyst (F) which was characterized by IR and X-ray crystallography.

CATALYST SYNTHESIS EXAMPLE 7

Synthesis of Catalyst (H)

This catalyst was made essentially the same as Catalyst (G) (Catalyst Synthesis Example 1) except that the starting material was 4,5-dimethyl-[N,N'-bis(3,5-di-tert-butylsalicylidenene)]-1,2-phenylenediamine.

CATALYST SYNTHESIS EXAMPLE 8

Synthesis of Catalyst (J)

The catalyst was made essentially the same as Catalyst (E$^1$) (Catalyst Synthesis Example 5), except that the starting material was (TPP) CrCl where TPP means tetraphenylporphyrin (TPP) CrCl is commercially available.

CARBONYLATION REACTION EXAMPLES I–XIII

Carbonylation reactions within the scope of the invention were carried out as follows for Examples I–VI. A 100 ml Parr reactor was dried at 90° C., under vacuum overnight. In a drybox, it was cooled in a −35° C. freezer for at least 1.5 hours and equipped with a small test-tube and magnetic stir bar. The test-tube was charged with 0.500 ml of compound (I) as described in Table 1 below, stored at −35° C., and catalyst as described in Table 1 below and amount thereof as described in Table 2 below. Upon removal from the drybox, the reactor was pressurized to pressure as described in Table 2 below, placed in a preheated oil bath and the reactor was stirred at temperature as set forth in Table 2 for amount of time as indicated in Table 2 below. When the indicated time had passed, the reactor was cooled in a bath of dry ice/acetone until the pressure reached a minimum and then slowly vented. The crude mixture was subjected to NMR analysis. Trapping of vented gases indicates that only 2–5% of the material is lost. Vented gases contained the same ratios of compounds (within 3–4%) that remained in the reactor. Results are set forth in Table 3 below.

Reaction conditions for the carbonylation reaction of Example VII were as follows and also include the conditions set forth in Table 2 below for Example VII: Using a gas-tight syringe, dry and degassed diglyme (20 ml) and propylene oxide (10 ml, 143 mmol) were injected into a 100 ml Parr pressure reactor equipped with a ball valve and a septum and previously charged, in a glovebox, with Catalyst (B) (0.13 g, 0.08 mmol). The reactor was pressured up to 1020 psi with carbon monoxide and stirred via the attached impeller at 75° C. for 21 hours at which point it was cooled to 3° C. in an ice bath and vented.

Reaction conditions for the carbonylation reaction of Example VIII were as follows and also included the conditions set forth in Table 2 below for Example VIII: Using an air-free graduated cylinder, 20 ml (285 mmol) propylene oxide was canulated into the above mentioned Parr reactor charged as above with 0.25 g (0.16 mmol) Catalyst (B). The reactor was pressured up to 810 psi with carbon monoxide and stirred at room temperature (22° C.) for 16 hours at which point it was cooled in an ice bath and vented.

Reaction conditions for the carbonylation reaction of Example IX were identical to those of Example VII except triglyme was used instead of diglyme and the scale was different (7 ml triglyme, 3.5 ml (50 mmol) propylene oxide, 0.15 g (0.09 mmol) Catalyst (B)) with the additional differences as set forth in Table 2 below.

Reaction conditions for the carbonylation reaction of Example X were identical to those of Example VIII except for the use of 0.07 g (0.09 mmol) Catalyst (B) and except for the differences set forth in Table 2 below.

Reaction conditions for the carbonylation reaction of Example XI were identical to those of Example VIII except for the use of 0.08 g (0.10 mmol) Catalyst ($E^2$) in place of Catalyst (B) and except for the differences set forth in Table 2 below.

Reaction conditions for the carbonylation reaction of Example XII were identical to those of Example VIII except for the use of 5 ml (71 mmol) propylene oxide and 0.05 g (0.04 mmol) Catalyst (F) in place of Catalyst (B) and except for the differences set forth in Table 2 below.

Results for Examples VII–XII are set forth in Table 3 below.

The carbonylation reaction for Example XIII was carried out as follows. A 100 ml Parr reactor equipped with a mechanical stirrer was heated at 80° C., under vacuum, overnight. The reactor was charged with propylene oxide and catalyst (D), (0.15 M solution in triglyme), in the drybox. Upon removal from the drybox, the reactor was pressured to 1,000 psi with carbon monoxide and heated at 80° C. with stirring for 16 hours. The catalyst was used in amount of 2 mole percent Co by weight of epoxide. After the 16 hours, the reactor was cooled in an ice bath until the pressure reached a minimum and then slowly vented. The crude mixture was subjected to NMR analysis. Catalyst and compound (I) are set forth in Table 1 below. Reaction conditions are set forth in Table 2 below. The results for Example XIII are set forth in Table 3 below.

The resulting β-lactone products were obtained as crude mixtures. Purification to obtain purified β-lactone products is readily carried out by vacuum distillation, flash column chromatography or other standard purification techniques.

Table 1 listing the catalyst and compound (I) for each of Examples I–XIII is set forth below:

TABLE 1

| Example | Catalyst | Compound (I) |
|---|---|---|
| I | G | R-propylene oxide |
| II | G | propylene oxide |
| III | G | 1-butene oxide |
| IV | G | epichlorohydrin |
| V | G | isobutylene oxide |
| VI | G | 2,3-epoxybutane |
| VII | B | propylene oxide |
| VIII | B | propylene oxide |
| IX | B | propylene oxide |
| X | $E^1$ | propylene oxide |
| XI | $E^2$ | propylene oxide |
| XII | F | propylene oxide |
| XIII | D | propylene oxide |

Table 2 listing for the reaction conditions for each of Examples I–XIII, is set forth below:

TABLE 2

| Example | time(h) | Pco (psi) | T (° C.) | Solvent | Compound (I) charged/catalyst charged (Co basis) (mole ratio) |
|---|---|---|---|---|---|
| I | 1 | 880 | 50 | neat | 100:1 |
| II | 1 | 880 | 50 | neat | 100:1 |
| III | 2.5 | 880 | 50 | neat | 100:1 |
| IV | 9.5 | 880 | 50 | neat | 100:1 |
| V | 1 | 880 | 50 | neat | 100:1 |
| VI | 7.5 | 880 | 75 | neat | 50:1 |
| VII | 21 | 1020 | 75 | diglyme | 1800:1 |
| VIII | 16 | 810 | 22 | neat | 1800:1 |
| IX | 12 | 870 | 75 | triglyme | 525:1 |
| X | 96 | 960 | 75 | neat | 3300:1 |
| XI | 95 | 940 | 75 | neat | 2900:1 |
| XII | 4 | 900 | 80 | neat | 1800:1 |
| XIII | 16 | 1000 | 80 | triglyme | 50:1 |

Co basis was used in defining Compound (I) charged/catalyst charged mole ratio because all the catalysts have the common feature of $Co(CO)_4$ anion so this provides standardization.

Table 3 presenting results for Examples I–XIII is set forth below where percent conversion and percent selectivity are as described previously and TON means turnover number and is moles compound (I) consumed divided by moles catalyst charged.

TABLE 3

| Example | Conversion (%) | Selectivity (%) | TON |
|---|---|---|---|
| I | 95 | >99 | 95 |
| II | 95 | >99 | 95 |
| III | 99 | >99 | 99 |
| IV | 73 | >99 | 73 |
| V | 83 | >99 | 83 |
| VI | 80 | 70 | 40 |
| VII | 72 | >95 | 1300 |
| VIII | 40 | >99 | 730 |
| IX | 90 | >99 | 460 |
| X | 69 | 80 | 2200 |
| XI | 52 | 85 | 1500 |
| XII | 86 | 96 | 1600 |
| XIII | 52 | 12 | 2 |

In Example I, the product was R-BBL.

In Example XIII, 6% acetone and 40% polymer were also produced.

CARBONYLATION REACTION EXAMPLES XIV–XXI

The carbonylation reactions of these examples were carried out in the presence of 5 mole % catalyst G (0.2 Mn DME) under a carbon monoxide pressure of 900 psi. In each case the compound (I) was present in amount of 1.92 mmol. The Example number, compound (I), temperature of reaction, time of reaction, product and yield obtained, are listed in Table 4 below:

TABLE 4

| Example | Substrate (I) | Temp (° C.) | Time. (h) | Products | Yield % |
|---|---|---|---|---|---|
| XIV | [epoxide structure] | 60 | 4 | [β-lactone structure] | 95 |
| XV | [epoxide structure] | 60 | 4 | [β-lactone structure] | 95 |
| XVI | [1,2-epoxybutane] | 60 | 4 | [β-lactone structure] | 99 |
| XVII | [1,2-epoxy-5-hexene] | 60 | 4 | [β-lactone structure] | 90 |
| XVIII | [epichlorohydrin] | 60 | 5 | [β-lactone structure] | 60 |
| XIX | [isobutylene oxide] | 50 | 3 | [two β-lactone structures (4:1)] | 90 |
| XX | [cis-2,3-epoxybutane (±)] | 60 | 10 | [β-lactone (±)] | 99 |
| XXI | [trans-2,3-epoxybutane] | 60 | 10 | [β-lactone (±)] | 75 |

The yields were determined by $^1$H NMR spectroscopy. The enantiomeric excess for Example XV was greater than 99% (R)-β-butyrolactone. The results for Examples XIV, XV, XVI, XVII, XVIII, XX and XXI were 100% regioselective, that is the insertion occurred at the less substituted carbon. In the cases of Examples XIX, insertion at the more substituted carbon is also present and the two products are shown. In Table 4, the compound (I) for Example XIV is propylene oxide, the compound (I) for Example XV is (R)-propylene oxide, the compound (I) for Example XVI is 1,2-epoxybutane, the compound (I) for Example XVII is 1,2-epoxy-5-hexene, the compound (I) for Example XVIII is epichlorohydrin, the compound (I) for Example XIX is isobutylene oxide, the compound (I) for Example XX is cis-2,3-epoxybutane and the compound (I) for Example XXI is trans-2,3-epoxybutane.

CARBONYLATION EXAMPLES XXII–XXV

The carbonylation reactions of these examples were carried out in the presence of 5 mole % catalyst (G) and for each substrate also with catalyst (H) (0.2M in DME) under a carbon monoxide pressure of 900 psi. In each case the compound (I) was present in amount of 1.92 mmol. The example number, compound (I), temperature of reaction, time of reaction, product and yield obtained, are listed in Table 5 below:

TABLE 5

| Example | Substrate (I) | Catalyst | Temp (°C.) | Time. (h) | Products | Yield % |
|---|---|---|---|---|---|---|
| XXII | 1-benzyl-2-methyl aziridine | G | 60 | 6 | β-lactam | 90 |
|  |  | H | 60 | 6 |  | 50 |
| XXIII | 7-benzyl-7-azabicyclo[4.1.0]heptane | G | 80 | 18 | bicyclic β-lactam (±) | 80 |
|  |  | H | 80 | 18 |  | <5 |
| XXIV | 1-tosyl-2-methylaziridine | G | 90 | 6 | N-tosyl β-lactam | 35 |
|  |  | H | 90 | 6 |  | 99 |
| XXV | cis-1-benzyl-2-(TBSO-methyl)-3-methylaziridine (±) | G | 60 | 5 | two β-lactam products (19:1) | 95 |

The yields were determined by $^1$H NMR spectroscopy. The results for Examples XXII, XXIII and XXIV were 100% regioselective. In the case of Example XXV, insertion at the more substituted carbon is also present and the two products are shown in Table 5. In Table 5, Ph is phenyl, Ts is tosyl and TBSO is tert-butyldimethylsilyloxy. The compound (I) for Example XXII is 1-benzyl-2-methyl aziridine, for Example XXIII is 7-benzyl-7-azabicyclo[4.1.0]heptane, for Example XXIV is 1-tosyl-2-methylaziridine and for Example XXV is cis-1-benzyl-2-(tert-butyldimethylsiloxymethyl)-3-methylaziridine.

CARBONYLATION EXAMPLE XXVI

Oxetane was carbonylated in the presence of 1 mole % catalyst ($E^1$) under a carbon monoxide pressure of 880 psi, neat, for 1.5 hours at 50° C. The product of interest was

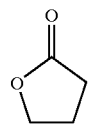

The percent conversion was about 30% (includes product of interest and other products).

CARBONYLATION EXAMPLE XXVII–XXXVII

These examples involve carbonylation of β-lactones according to the following reaction equation:

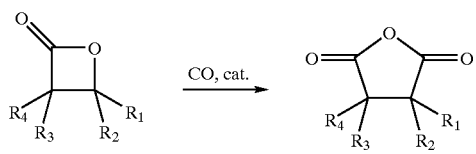

The starting materials, reaction conditions and results are given in Table 6 below. In respect to the starting materials, in each case $R_1$ and $R_4$ are H.

TABLE 6

| Example | $R_3$ | $R_2$ | Catalyst and its amount | Solvent | Time (h) | Temp. (°C.) | Conversion % |
|---|---|---|---|---|---|---|---|
| XXVII | H | Me | $E^1$, 1% | DME | 5 | 80 | 35 |
| XXVIII | H | Me | $E^1$, 2% | DME | 5 | 80 | 65 |

TABLE 6-continued

| Example | $R_3$ | $R_2$ | Catalyst and its amount | Solvent | Time (h) | Temp. (° C.) | Conversion % |
|---|---|---|---|---|---|---|---|
| XXIX | H | Me | $G^1$, 5% | DME | 5 | 80 | 60 |
| XXX | H | Me | $G^1$, 5% | DME | 14 | 80 | >90 |
| XXXI | H | Me | $E^1$, 1% | — | 8 | 80 | 80 |
| XXXII | H | Me | $E^1$, 1% | — | 24 | 80 | 84 |
| XXXIII | H | Me | $G^2$, 2% | DME | 20 | 50 | 85 |
| XXXIV | H | Et | $G^1$, 5% | DME | 10 | 80 | 70 |
| XXXV | H | $CCl_3$ | $G^1$, 5% | DME | 24 | 75 | — |
| XXXVI | Me | H | $G^1$, 5% | DME | 5 | 80 | 95 |
| XXXVII | Ph | H | $G^1$, 5% | DME | 10 | 80 | 80 |

In the above table, Me is methyl, Et is ethyl, Ph is phenyl and DME is dimethoxyethane.

CARBONYLATION EXAMPLE XXXVIII

The compound (I) was benzyl glycidyl ether. The benzyl glycidyl ether was carbonylated in the presence of 1 mole % catalyst (H), neat, under a carbon monoxide pressure of 800 psi for 15 hours at 50° C.

CARBONYLATION EXAMPLE XXXIX, XL and XLI

For Example XXXIX, the compound (I) was 1-buteneoxide. For Example XL the compound (I) was 1-heptene oxide. For Example XLI, the compound (I) was cyclooctene oxide. In each case the compound (I) was carbonylated in the presence of 0.4 mole % catalyst (J), neat, under a carbon monoxide pressure of 1,000 psi for 20 hours at 60° C. The product of Carbonylation Example XLI was 9-oxa-bicyclo[6.2.0]decan-10-one and has the structure:

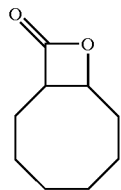

CARBONYLATION EXAMPLE XLII

The compound (I) was cyclododecene oxide. The cyclododecene oxide was carbonylated in the presence of 1.67 mole % catalyst (G), neat, under a carbon monoxide pressure of 1400 psi for 6 hours at 50° C. The product was 13-oxa-bicyclo[10.2.0]tetradecan-14-one and has the structure:

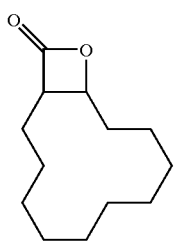

CARBONYLATION EXAMPLE XLIII

The compound (I) was:

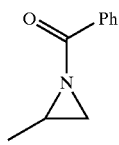

The compound (I) was carbonylated in the presence of 5 mole % catalyst ($G^1$), in dimethoxyethane under a carbon monoxide pressure of 900 psi for 4 hours at 50° C. The reaction product was a mixture of the two isomeric oxazinones:

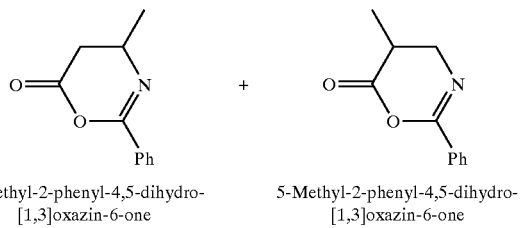

| 4-Methyl-2-phenyl-4,5-dihydro-[1,3]oxazin-6-one | 5-Methyl-2-phenyl-4,5-dihydro-[1,3]oxazin-6-one |
|---|---|
| 70 | 30 |

Variations

Many variations will be obvious to those skilled in the art. Thus, tie scope of the invention is defined by the claims.

What is claimed is:

1. A process for the carbonylation of a compound having the formula:

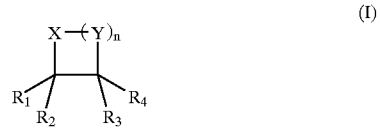
(I)

where $R_1$, $R_2$, $R_3$ and $R_4$ are selected from the group consisting of hydrogen, $C_1$–$C_{100,000}$-alkyl, $C_2$–$C_{100,000}$-alkenyl and $C_6$–$C_{100,000}$-aryl, where the alkyl, alkenyl and aryl are optionally substituted with halogen or benzyl ether, and alkylaryl, ester, ketone, alcohol, acid, aldehyde, amide and tosyl containing from 1 to 20 carbon atom, and benzyl ether, alkyl substituted silyl ether where the ether group is $C_1$–$C_6$ alkylene and alkyl substitution consists of one to three $C_1$–$C_6$ alkyl(s) substituted on silyl, and any other functionality that the catalyst referred to below is tolerant of, and where $R_2$ and $R_4$ can join to form a ring, and X is selected from the group consisting of O, S and $NR_5$ where $R_5$ is selected from the group consisting of hydrogen, $C_1$–$C_{100,000}$-alkyl, $C_2$–$C_{100,000}$-alkenyl and $C_6$–$C_{100,000}$-aryl where the alkyl alkenyl and aryl are optionally substituted with halogen or benzyl ether, and alkylaryl, ester, ketone, alcohol, acid, aldehyde, amide and tosyl containing from 1 to 20 carbon atoms, and benzyl ether, alkyl substituted silyl ether where the ether group is $C_1$–$C_6$-alkylene and where the alkyl substitution consists of one to three $C_1$–$C_6$ alkyl(s) substituted on silyl, and any other functionality that the catalyst referred to below is tolerant of and does not cause rearrangement, and where n is 0 or 1, and Y is C=O or $CH_2$, said process comprising the step of reacting compound (I) with carbon monoxide in the presence of a catalytically effective amount of catalyst having the general formula [Lewis acid]$^{z+}${[QM(CO)$_x$]$^{w-}$}$_y$ where Q is any ligand and need not be present, M is a transition metal selected from the group consisting of Groups 4, 5, 6, 7, 8, 9 and 10 of the periodic table of elements, z is the valence of the Lewis acid and ranges from 1 to 6, w is the charge of the metal carbonyl and ranges from 1 to 4 and y is a number such that w times y equals z, and x is a number such as to provide a stable anionic metal carbonyl for {[QM(CO)$_x$]$^{w-}$}$_y$, to form a product having the structural formula:

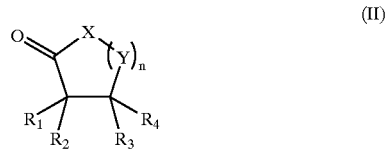
(II)

where $R_1$, $R_2$, $R_3$ and $R_4$ and X correspond to $R_1$, $R_2$, $R_3$, $R_4$ and X in (I) including $R_2$ and $R_4$ forming a ring if that is the case for (I); and in the case where n for (I) is 0, n for (II) is 0 or 1, and in the case where n for (I) is 1, n for (II) is 1; said catalyst excluding catalyst formed from the combination of a cobalt source and a hydroxy substituted pyridine.

2. The process of claim 1 where n for (I) is 0 so that the structural formula for (I) becomes:

(III)

and the product has the structural formula:

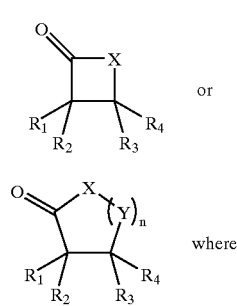
(IV)

or (II)

where n is 1 and Y is C=O.

3. The process of claim 2 where the catalyst is [(salph)Al(THF)$_2$][Co(CO)$_4$] where THF is tetrahydrofuran and which has the structural formula:

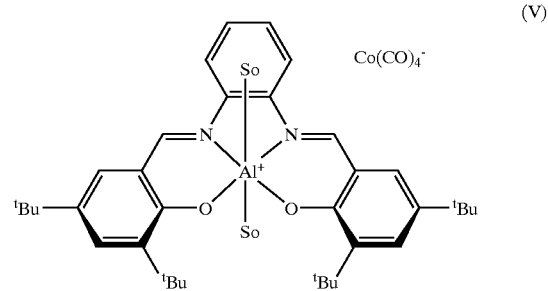
(V)

where So is tetrahydrofuran and $^t$Bu is t-butyl.

4. The process of claim 3 wherein the reaction is carried out at a carbon monoxide pressure ranging from 100 to 10,000 psi and a temperature ranging from 0° to 120° C. in the presence of catalyst in a mole ratio of compound (III) to catalyst (cobalt basis) ranging from 1:1 to 10,000:1.

5. The process of claim 4 where X for (III) is O.

6. The process of claim 4 where the compound (III) is propylene oxide.

7. The process of claim 4 where the compound (III) is (R)-propylene oxide and the product is (R)-β-butyrolactone.

8. The process of claim 7 where the reaction is carried out at a pressure ranging from 850 to 900 psi and a temperature ranging from 0 to 120° C., over a time period ranging from 0.75 to 1.5 hours.

9. The process of claim 4 where the compound (III) is 1-butene oxide.

10. The process of claim 4 where the compound (III) is epichlorohydrin.

11. The process of claim 4 where the compound (III) is isobutylene oxide.

12. The process of claim 4 where the compound (III) is 2,3-epoxybutane.

13. The process of claim 4 where X is $NR_5$.

14. The process of claim 13 where the compound (III) is 1-benzyl-2-methyl aziridine.

15. The process of claim 13 where the compound (III) is 1-tosyl-2-methylaziridine.

16. The process of claim 13 where the compound (III) is cis-1-benzyl-2-(tert-butyldimethylsiloxymethyl)-3-methyl aziridine.

17. The process of claim 2 where the catalyst is

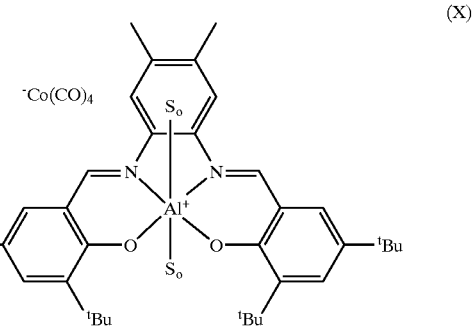
(X)

where $^t$Bu is t-butyl and So is tetrahydrofuran.

18. The process of claim 17 where the reaction is carried out at a carbon monoxide pressure ranging from 100 to 10,000 psi and a temperature ranging from 0° C. to 120° C. in the presence of catalyst in a mole ratio of compound (III) to catalyst (cobalt basis ranging from 1:1 to 10,000:1.

19. The process of claim 18 where X for (III) is O.

20. The process of claim 19 where the compound (III) is benzyl glycidyl ether.

21. The process of claim 2 where the catalyst is

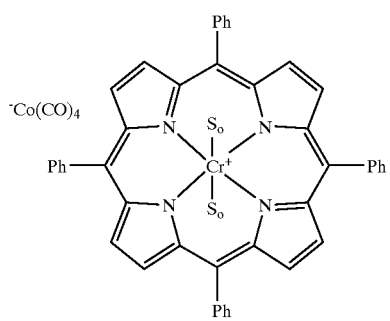

(XI)

where So is tetrahydrofuran and Ph is phenyl.

22. The process of claim 21 where the reaction is carried out at a carbon monoxide pressure ranging from 100 to 10,000 psi and a temperature ranging from 0° C. to 120° C. in the presence of catalyst in a mole ratio of compound (III) to catalyst (cobalt basis) ranging from 1:1 to 10,000:1.

23. The process of claim 22 where X for (III) is O.

24. The process of claim 23 where the compound (III) is 1-butene oxide.

25. The process of claim 23 where the compound (III) is 1-heptene oxide.

26. The process of claim 23 where the compound (III) is cyclooctene oxide.

27. The process of claim 2 where the catalyst has the structure

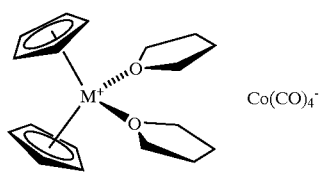

(VI)

where M is a metal such that (VI) is stable.

28. The process of claim 27 where the catalyst has the structure (VI) where M is titanium with a valence of three.

29. The process of claim 28 where the reaction is carried out at a carbon monoxide pressure ranging from 100 to 10,000 psi and a temperature ranging from 0° C. to 120° C. in the presence of a catalyst in a mole ratio of compound (III) to catalyst (cobalt basis) ranging from 1:1 to 10,000:1.

30. The process of claim 29 where X for the compound (III) is O.

31. The process of claim 30 where the compound (III) is propylene oxide.

32. The process of claim 31 where the compound (III) is R-propylene oxide.

33. The process of claim 30 where the compound (III) is 1,2-epoxybutane.

34. The process of claim 30 where the compound (III) is 1,2-epoxy-5-hexene.

35. The process of claim 30 where the compound (III) is epichlorohydrin.

36. The process of claim 30 where the compound (III) is isobutylene oxide.

37. The process of claim 30 where the compound (III) is cis-2,3-epoxybutane.

38. The process of claim 30 where the compound (III) is trans-2,3-epoxybutane.

39. The process of claim 29 where X for the compound (III) is $NR_5$.

40. The process of claim 39 where the compound (III) is 1-benzyl-2-methyl aziridine.

41. The process of claim 39 where the compound (III) is 7-benzyl-7-azabicyclo[4.1.0]heptane.

42. The process of claim 39 where the compound (III) is 1-tosyl-2-methylaziridine.

43. The process of claim 39 where the compound (III) is cis-1-benzyl-2-(tert-butylmethylsilyloxymethyl)-3-methylaziridine.

44. The process of claim 1 where n for (I) is 1 and Y is C=O or $CH_2$.

45. The process of claim 44 where the catalyst has the structure

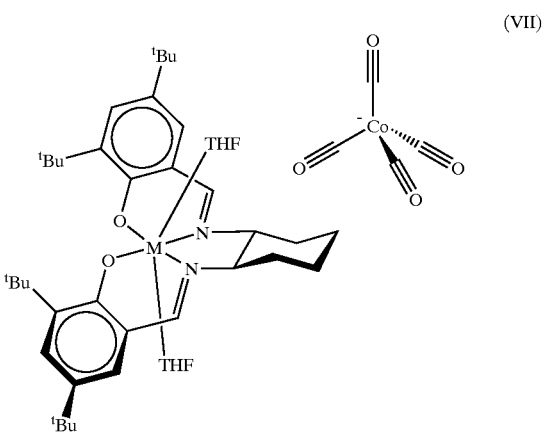

(VII)

where THF is tetrahydrofuran and $^t$Bu is t-butyl and M is Al.

46. The process of claim 45 where the reaction is carried out at a carbon monoxide pressure ranging from 100 to 10,000 psi and a temperature ranging from 0° C. to 120° C. in the presence of a catalyst in a mole ratio of compound (I) to catalyst (cobalt basis) ranging from 1:1 to 10,000:1.

47. The process of claim 46 where the compound (I) is oxetane.

48. The process of claim 46 where Y is C=O and $R_1$ and $R_3$ for the compound (I) are both H.

49. The process of claim 48 where $R_4$ for the compound (I) is H.

50. The process of claim 49 where $R_2$ for the compound (I) is Me.

51. The process of claim 44 where the catalyst has the structure

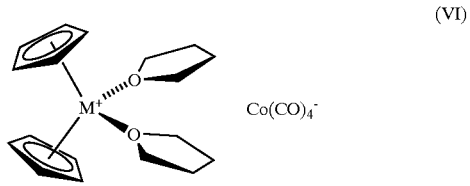

(VI)

where M is titanium with a valence of three.

52. The process of claim 51 where the reaction is carried out at a carbon monoxide pressure ranging from 100 to 10,000 psi and a temperature ranging from 0° C. to 120° C. in the presence of a catalyst in a mole ratio of compound (I) to catalyst (cobalt basis) ranging from 1:1 to 10,000:1.

53. The process of claim 52 where Y is C=O.

54. The process of claim 53 where $R_1$, $R_3$ and $R_4$ for the compound (I) are H.

55. The process of claim 54 where $R_2$ for the compound (I) is Me.

56. The process of claim 54 where $R_2$ for the compound (I) is Et.

57. The process of claim 54 where $R_2$ for the compound (I) is $CCl_3$.

58. The process of claim 52 where $R_1$, $R_2$ and $R_4$ for the compound (I) are H.

59. The process of claim 58 where $R_3$ for the compound (I) is Me.

60. The process of claim 58 where $R_3$ for the compound (I) is Ph.

61. The process of claim 44 where the catalyst has the structure

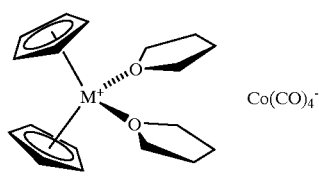

(VI)

where M is samarium with a valence of three.

62. The process of claim 61 where the reaction is carried out at a carbon monoxide pressure ranging from 100 to 10,000 psi and a temperature ranging from 0° C. to 120° C. in the presence of a catalyst in a mole ratio of compound (I) to catalyst (cobalt basis) ranging from 1:1 to 10,000:1.

63. The process of claim 62 where Y is C=CO and $R_1$, $R_3$ and $R_4$ for the compound (I) are H and $R_2$ for the compound (I) is Me.

64. The process of claim 1 where in the [Lewis acid]$^{z+}$ portion of the catalyst a neutral two electron donor is present and fills the coordination valence of the cationic Lewis acid.

65. The process of claim 64 where the [Lewis acid]$^{z+}$ portion of the catalyst contains an aluminum or chromium center.

66. The process claim 65 where the neutral two electron donor is tetrahydrofuran.

67. The process of claim 1 where the catalyst has the structure

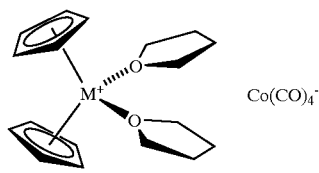

(VI)

where M is a metal such that (VI) is stable.

68. The process of claim 67 where the reaction is carried out at a carbon monoxide pressure ranging from 100 to 10,000 psi and a temperature ranging from 0° C. to 120° C. in the presence of a catalyst in a mole ratio of compound (I) to catalyst (cobalt basis) ranging from 1:1 to 10,000:1.

69. A process for the carbonylation of a compound having the formula

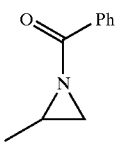

(XI)

where Ph is phenyl, said process comprising the step of reacting compound (XI) with carbon monoxide in the presence of a catalytically effective amount of catalyst having the general formula [Lewis acid]$^{z+}\{[QM(CO)_x]^{w-}\}_y$ where Q is any ligand and need not be present, M is a transition metal selected from the group consisting of Groups 4, 5, 6, 7, 8, 9 and 10 of the periodic table of elements, z is the valence of the Lewis acid and ranges from 1 to 6, w is the charge of the metal carbonyl and ranges from 1 to 4 and y is a number such that w times y equals z, and x is a number such as to provide a stable anionic metal carbonyl for $\{[QM(CO)_x]^{w-}\}_y$, to form a product which comprises a mixture of

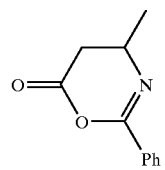

and

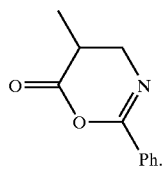

70. A compound having the structural formula:

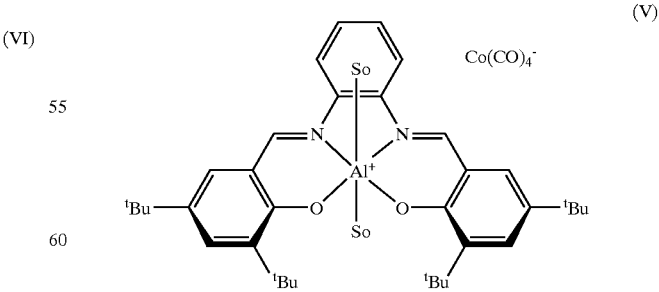

(V)

where $^tBu$ is t-butyl and So is a neutral two electron donor.

71. The compound of claim 70 where the neutral two electron donor is tetrahydrofuran.

72. A compound having the structural formula:

(VIII)

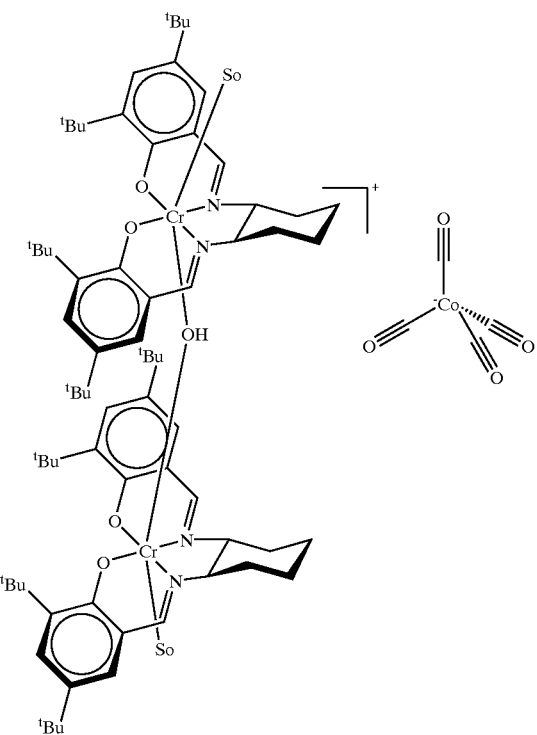

where the 'Bu is t-butyl and So is a neutral two electron donor.

73. The compound of claim 72 where the neutral two electron donor is tetrahydrofuran.

74. A compound having the structural formula:

(IX)

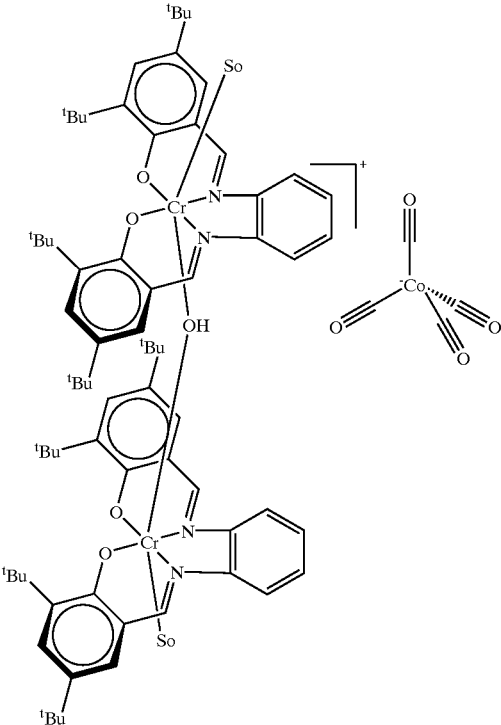

where 'Bu is t-butyl and So is a neutral two electron donor.

75. The compound of claim 74 where the neutral two electron donor is tetrahydrofuran.

76. A compound having the structure:

(VII)

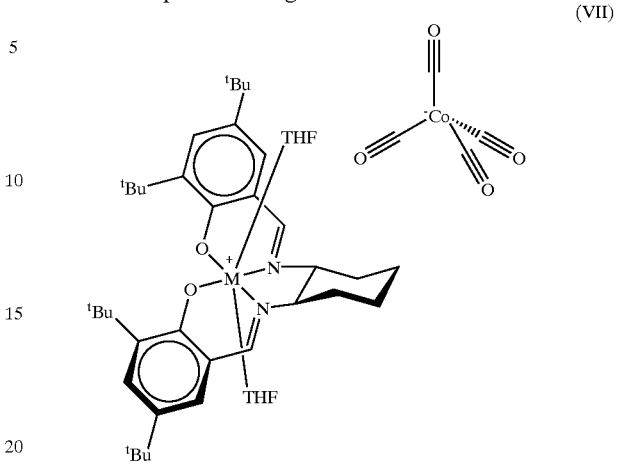

where THF is tetrahydrofuran and 'Bu is t-butyl.

77. The compound of claim 76 where M is Al.
78. The compound of claim 76 where M is Cr.
79. A compound having the structure:

(X)

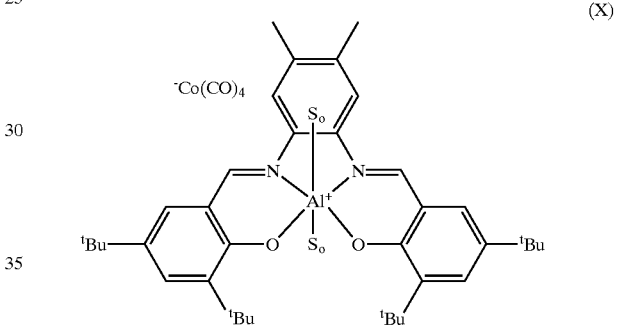

where 'Bu is t-butyl and So is a neutral two electron donor.

80. The compound of claim 79 where the neutral two electron donor is tetrahydrofuran.

81. A compound having the structure:

(XI)

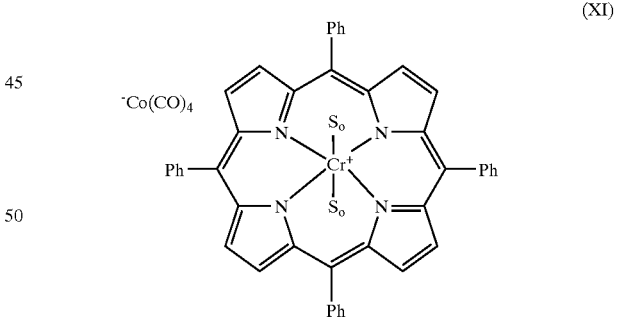

where Ph is phenol and So is a neutral two electron donor.

82. The compound of claim 81 where the neutral two electron donor is tetrahyrofuran.

83. 9-Oxa-bicyclo[6.2.0]decan-10-one.
84. 13-Oxa-bicyclo[10.2.0]tetradecan-14-one.
85. The process of claim 1 where the [Lewis acid]$^{z+}$ portion of the catalyst does not contain a neutral two electron donor.
86. The process of claim 7 where the yield of (R)-β-butyrolactone is greater than 95%.
87. The process of claim 1 wherein in the formula (I), at least one of $R_1$, $R_2$, $R_3$ and $R_4$ is not hydrogen.

* * * * *

UNITED STATES PATENT AND TRADEMARK OFFICE
CERTIFICATE OF CORRECTION

PATENT NO. : 6,852,865 B2
DATED : February 8, 2005
INVENTOR(S) : Geoffrey W. Coates and Yutan D. Y. L. Getzler Page 1 of 1

It is certified that error appears in the above-identified patent and that said Letters Patent is hereby corrected as shown below:

Column 34,
Line 26, in the formula (VII)) the, "M" should read -- $M^+$ --.

Signed and Sealed this

Twenty-fourth Day of May, 2005

JON W. DUDAS
*Director of the United States Patent and Trademark Office*